US012635879B2

(12) United States Patent
Yamada et al.

(10) Patent No.: US 12,635,879 B2
(45) Date of Patent: May 26, 2026

(54) OPHTHALMIC OBSERVATION APPARATUS

(71) Applicant: Topcon Corporation, Tokyo (JP)

(72) Inventors: Kazuhiro Yamada, Tokyo (JP);
Kazuhiro Oomori, Tokyo (JP);
Yasufumi Fukuma, Wako (JP)

(73) Assignee: TOPCON CORPORATION, Tokyo
(JP)

( * ) Notice: Subject to any disclaimer, the term of this
patent is extended or adjusted under 35
U.S.C. 154(b) by 284 days.

(21) Appl. No.: 18/033,812

(22) PCT Filed: Dec. 9, 2020

(86) PCT No.: PCT/JP2020/045761
§ 371 (c)(1),
(2) Date: Apr. 26, 2023

(87) PCT Pub. No.: WO2022/091431
PCT Pub. Date: May 5, 2022

(65) Prior Publication Data
US 2024/0008741 A1     Jan. 11, 2024

Related U.S. Application Data

(60) Provisional application No. 63/106,087, filed on Oct.
27, 2020.

(51) Int. Cl.
A61B 3/13        (2006.01)
A61B 3/117       (2006.01)
(Continued)

(52) U.S. Cl.
CPC ................ A61B 3/13 (2013.01); A61B 3/117
(2013.01); A61B 3/12 (2013.01); A61B 3/14
(2013.01);
(Continued)

(58) Field of Classification Search
CPC .. A61B 3/13; A61B 3/117; A61B 3/12; A61B
3/14; A61B 3/145; A61B 3/15;
(Continued)

(56) References Cited

U.S. PATENT DOCUMENTS 5,579,772 A     12/1996  Kinukawa et al.
10,251,783 B2    4/2019  Chernyak
(Continued)

FOREIGN PATENT DOCUMENTS

CN        101268928 A      9/2008
CN        103784117 A      5/2014
(Continued)

OTHER PUBLICATIONS

Extended European Search Report issued Nov. 5, 2024, in corre-
sponding European Patent Application No. 20959942.2, 8pp.
(Continued)

*Primary Examiner* — William R Alexander
*Assistant Examiner* — Mackenzi Waddell
(74) *Attorney, Agent, or Firm* — XSENSUS LLP

(57)                    ABSTRACT

An ophthalmic observation apparatus of an embodiment
includes an illumination system, a photography system, and
a focus processor. The illumination system includes a light
source configured to emit illumination light and an indicator
member having a plurality of indicators, and is configured to
project the illumination light onto a subject's eye via the
indicator member. The photography system includes an
image sensor and is configured to perform photography of
the subject's eye. The focus processor is configured to
perform detection of a plurality of indicator images from an
image acquired by the photography system, and perform a
focus control of the photography system based on the
plurality of indicator images.

17 Claims, 13 Drawing Sheets

(51) Int. Cl.

| | |
|---|---|
| *A61B 3/12* | (2006.01) |
| *A61B 3/14* | (2006.01) |
| *A61B 3/15* | (2006.01) |
| *A61B 90/00* | (2016.01) |
| *G02B 21/00* | (2006.01) |
| *G02B 21/36* | (2006.01) |
| *G06T 7/00* | (2017.01) |
| *H04N 23/67* | (2023.01) |
| *H04N 23/71* | (2023.01) |
| *H04N 23/74* | (2023.01) |
| *H04N 23/76* | (2023.01) |

(52) U.S. Cl.
CPC ............... *A61B 3/145* (2013.01); *A61B 3/15* (2013.01); *A61B 3/152* (2013.01); *G02B 21/0012* (2013.01); *G02B 21/365* (2013.01); *G06T 7/0012* (2013.01); *G06T 7/97* (2017.01); *H04N 23/67* (2023.01); *H04N 23/71* (2023.01); *H04N 23/74* (2023.01); *H04N 23/76* (2023.01); *A61B 2090/0807* (2016.02); *G06T 2207/10016* (2013.01); *G06T 2207/10056* (2013.01); *G06T 2207/30041* (2013.01); *G06T 2207/30168* (2013.01)

(58) Field of Classification Search
CPC ...... A61B 3/152; A61B 5/00; G02B 21/0012; G02B 21/365; G02B 21/367
See application file for complete search history.

(56) References Cited

U.S. PATENT DOCUMENTS

| | | | |
|---|---|---|---|
| 10,369,053 B2 | 8/2019 | Srinivasan et al. | |
| 2002/0026179 A1 | 2/2002 | Toh | |
| 2004/0004694 A1 | 1/2004 | Sugino et al. | |
| 2005/0073647 A1 | 4/2005 | Mihashi et al. | |
| 2006/0247659 A1 | 11/2006 | Moeller et al. | |
| 2007/0047072 A1 | 3/2007 | Zimmer | |
| 2008/0123053 A1 | 5/2008 | Mihashi et al. | |
| 2008/0198219 A1 | 8/2008 | Yoshida et al. | |
| 2009/0122398 A1 | 5/2009 | Machida et al. | |
| 2009/0190092 A1 | 7/2009 | Tsukada et al. | |
| 2009/0244483 A1* | 10/2009 | Yoshino | A61B 3/14 351/206 |
| 2011/0122365 A1 | 5/2011 | Kraus et al. | |
| 2011/0153013 A1 | 6/2011 | Moeller et al. | |
| 2011/0157553 A1 | 6/2011 | Moeller et al. | |
| 2011/0230751 A1 | 9/2011 | Kersting | |
| 2011/0292340 A1 | 12/2011 | Shimizu et al. | |
| 2011/0304819 A1 | 12/2011 | Juhasz et al. | |
| 2012/0050672 A1* | 3/2012 | Aikawa | A61B 3/14 351/206 |
| 2012/0197102 A1 | 8/2012 | Hanebuchi et al. | |
| 2013/0110092 A1 | 5/2013 | Yee | |
| 2013/0110093 A1 | 5/2013 | Yee | |
| 2013/0110206 A1 | 5/2013 | Yee et al. | |
| 2013/0116672 A1 | 5/2013 | Yee | |
| 2013/0135582 A1 | 5/2013 | Hanebuchi et al. | |
| 2014/0118687 A1 | 5/2014 | Ohban et al. | |
| 2014/0146287 A1 | 5/2014 | Ota | |
| 2014/0160429 A1* | 6/2014 | Nakano | A61B 3/14 351/246 |
| 2014/0228824 A1 | 8/2014 | Yee et al. | |
| 2014/0300863 A1* | 10/2014 | Fukuma | A61B 3/152 351/205 |
| 2015/0046094 A1 | 2/2015 | Chaudhary et al. | |
| 2015/0077528 A1 | 3/2015 | Awdeh | |
| 2015/0272435 A1 | 10/2015 | Ito et al. | |
| 2015/0342460 A1 | 12/2015 | Izatt et al. | |
| 2016/0095752 A1 | 4/2016 | Srinivasan et al. | |
| 2016/0128871 A1 | 5/2016 | Yee | |
| 2016/0157710 A1* | 6/2016 | Tomatsu | A61B 3/14 351/206 |

| | | | |
|---|---|---|---|
| 2016/0228295 A1 | 8/2016 | Yee et al. | |
| 2016/0291257 A1* | 10/2016 | Huang | G02B 21/0004 |
| 2017/0151089 A1 | 6/2017 | Chernyak | |
| 2017/0280989 A1 | 10/2017 | Heeren | |
| 2017/0281405 A1 | 10/2017 | Ha | |
| 2017/0303782 A1 | 10/2017 | Ito et al. | |
| 2017/0304119 A1 | 10/2017 | Yee | |
| 2018/0049840 A1 | 2/2018 | Awdeh | |
| 2018/0098812 A1 | 4/2018 | Ootsuki | |
| 2018/0125361 A1 | 5/2018 | Okuda | |
| 2018/0228431 A1 | 8/2018 | Chaudhary et al. | |
| 2019/0076012 A1 | 3/2019 | Kobayashi | |
| 2019/0091008 A1 | 3/2019 | Ishikawa | |
| 2019/0104921 A1 | 4/2019 | Yamamoto | |
| 2019/0192251 A1 | 6/2019 | Kado et al. | |
| 2019/0357980 A1 | 11/2019 | Andrews et al. | |
| 2020/0146885 A1 | 5/2020 | Ootsuki et al. | |
| 2020/0214562 A1 | 7/2020 | Kawasaki et al. | |
| 2020/0237213 A1 | 7/2020 | Ono et al. | |
| 2020/0306002 A1 | 10/2020 | Kamata | |
| 2020/0311918 A1 | 10/2020 | Loerner | |
| 2021/0401369 A1 | 12/2021 | Chaudhary et al. | |
| 2022/0115122 A1 | 4/2022 | Enoki et al. | |
| 2022/0148165 A1 | 5/2022 | Ootsuki et al. | |
| 2022/0386869 A1 | 12/2022 | Ono et al. | |

FOREIGN PATENT DOCUMENTS

| | | |
|---|---|---|
| CN | 104939802 A | 9/2015 |
| DE | 202013011877 U1 | 9/2014 |
| EP | 3491996 A1 | 6/2019 |
| JP | 2001-276111 A | 10/2001 |
| JP | 3354627 B2 | 12/2002 |
| JP | 2003-310556 A | 11/2003 |
| JP | 2006136714 A | 6/2006 |
| JP | 2006280612 A | 10/2006 |
| JP | 2007-028295 A | 2/2007 |
| JP | 2009-118955 A | 6/2009 |
| JP | 2011191517 A | 9/2011 |
| JP | 2011528592 A | 11/2011 |
| JP | 2012506272 A | 3/2012 |
| JP | 2012152469 A | 8/2012 |
| JP | 2013-027672 A | 2/2013 |
| JP | 2014068766 A | 4/2014 |
| JP | 2014-534011 A | 12/2014 |
| JP | 2016-182262 A | 10/2016 |
| JP | 2016531666 A | 10/2016 |
| JP | 2016209291 A | 12/2016 |
| JP | 2016214781 A | 12/2016 |
| JP | 2017-012430 A | 1/2017 |
| JP | 2017029333 A | 2/2017 |
| JP | 2018-051210 A | 4/2018 |
| JP | 2018051223 A | 4/2018 |
| JP | 2019-013803 A | 1/2019 |
| JP | 2019-092844 A | 6/2019 |
| JP | 2019-162336 A | 9/2019 |
| JP | 2020-116140 A | 8/2020 |
| JP | 2020-130607 A | 8/2020 |
| WO | 03/022138 A1 | 3/2003 |
| WO | 2016/061454 A1 | 4/2016 |
| WO | 2017/154348 A1 | 9/2017 |
| WO | 2017175853 A1 | 10/2017 |
| WO | 2017/221507 A1 | 12/2017 |
| WO | 2018/207466 A1 | 11/2018 |
| WO | 2019/059314 A1 | 3/2019 |
| WO | 2020/179588 A1 | 9/2020 |

OTHER PUBLICATIONS

Extended European Search Report issued Nov. 7, 2024, in corresponding European Patent Application No. 20959943.0, 8pp.
Extended European Search Report issued Nov. 5, 2024, in corresponding European Patent Application No. 20959945.5, 9pp.
Chinese Office Action issued Dec. 20, 2024, in corresponding Chinese Patent Application No. 202080106764.2, 15pp.
Chinese Office Action issued Dec. 24, 2024, in corresponding Chinese Patent Application No. 202080106762.3, 18pp.

(56)          References Cited

OTHER PUBLICATIONS

Chinese Office Action issued Dec. 31, 2024, in corresponding Chinese Patent Application No. 202080106760.4, 12pp.
Japanese Office Action issued Jan. 28, 2025, in corresponding Japanese Patent Application No. 2022-558820, 11pp.
Office Action issued on Apr. 28, 2025, in corresponding European patent Application No. 21885560.9, 9 pages.
Office Action issued on Jun. 10, 2025, in corresponding European patent Application No. 20959945.5, 7 pages.
Office Action issued on Jun. 27, 2025, in corresponding European patent Application No. 20959942.2, 8 pages.
Office Action issued on Jun. 12, 2025, in corresponding Chinese patent Application No. 202080106760.4, 10 pages.
International Search Report and Written Opinion mailed on Mar. 2, 2021, received for PCT Application PCT/JP2020/045755, filed on Dec. 9, 2020, 8 pages including English Translation.
International Search Report and Written Opinion mailed on Jan. 19, 2021, received for PCT Application PCT/JP2020/045761, filed on Dec. 9, 2020, 10 pages including English Translation.
International Search Report and Written Opinion mailed on Feb. 2, 2021, received for PCT Application PCT/JP2020/045760, filed on Dec. 9, 2020, 9 pages including English Translation.
International Search Report and Written Opinion mailed on Mar. 9, 2021, received for PCT Application PCT/JP2020/045754, filed on Dec. 9, 2020, 9 pages including English Translation.
International Search Report and Written Opinion mailed on Mar. 23, 2021, received for PCT Application PCT/JP2021/003639, filed on Feb. 2, 2021, 8 pages including English Translation.
Japanese Office Action issued Aug. 20, 2024, in corresponding Japanese Application No. JP 2022-558821, 6pp.
Japanese Office Action issued Sep. 3, 2024, in corresponding Japanese Application No. JP 2022-558822, 6pp.
Japanese Office Action issued Oct. 22, 2024, in corresponding Japanese Application No. JP 2022-558823, 6pp.
Japanese Office Action issued Aug. 27, 2024, in corresponding Japanese Application No. JP 2022-558830, 6pp.
Extended European Search Report issued Sep. 18, 2024, in corresponding European Application No. 21885560.9, 8pp.
Japanese Office Action issued Jun. 18, 2025, in corresponding Japanese Patent Application No. 2022-558823, 6pp.
Office Action issued Nov. 14, 2025, in corresponding U.S. Appl. No. 18/033,821, 17pp.

Communication pursuant to Article 94(3) EPC issued Oct. 1, 2025, in corresponding European Patent Application No. 21 885 560.9, 7pp.
Communication pursuant to Article 94(3) EPC issued Jul. 10, 2025 in corresponding European Patent Application No. 20 959 943.0, 7pp.
Chinese Office Action issued Jul. 30, 2025, in corresponding Chinese Patent Application No. 202080106764.2, with Machine Translation by Global Dossier, 10pp.
Japanese Office Action issued Aug. 5, 2025, in corresponding Japanese Patent Application No. 2024-212100, with Machine Translation by Global Dossier, 10pp.
US Office Action issued Jul. 28, 2025 in related U.S. Appl. No. 18/033,802, 68pp.
US Office Action issued Jul. 2, 2025 in related U.S. Appl. No. 18/033,815, 66pp.
US Office Action issued Jul. 2, 2025 in related U.S. Appl. No. 18/033,821, 25pp.
US Office Action issued Jun. 12, 2025 in related U.S. Appl. No. 18/033,849, 8pp.
Communication pursuant to Article 94(3) EPC issued Nov. 7, 2025, in corresponding European Patent Application No. 20 959 945.5, 5pp.
Office Action issued Dec. 5, 2025, in corresponding U.S. Appl. No. 18/033,849, 9pp.
Communication pursuant to Article 94(3) EPC issued Dec. 8, 2025, in corresponding European Patent Application No. 20 959 942.2, 10pp.
Office Action issued Dec. 8, 2025, in corresponding U.S. Appl. No. 18/033,802, 14pp.
Communication pursuant to Article 94(3) EPC issued Dec. 12, 2025, in corresponding European Patent Application No. 20 959 943.0, 4 pp.
Office Action issued Dec. 16, 2025, in corresponding U.S. Appl. No. 18/033,815, 17pp.
Office Action issued Jan. 20, 2026, in corresponding Japanese Patent Application No. 2024-212100, 12pp.
Chinese Office Action issued Feb. 6, 2026, in Chinese Patent Application No. 202080106760.4, 8pp.
Chinese Office Action issued Feb. 11, 2026, in Chinese Patent Application No. 202180073485.5, 16pp.
US Office Action issued Apr. 2, 2026, in related U.S. Appl. No. 18/033,815.

* cited by examiner

OPHTHALMIC OBSERVATION APPARATUS

CROSS-REFERENCE TO RELATED APPLICATIONS

This application is a national stage (under 35 U.S.C. 371) of International Patent Application No. PCT/JP2020/045761, filed Dec. 9, 2020. claiming priority to U.S. Provisional Patent Application Ser. No. 63/106,087, filed Oct. 27, 2020, entitled "APPARATUS AND METHOD FOR OPHTHALMIC OBSERVATION", both of which are herein incorporated by reference in their entirety.

FIELD

The present disclosure relates generally to an ophthalmic observation apparatus.

BACKGROUND

An ophthalmic observation apparatus is an apparatus for observing an eye of a patient (which will be referred to as a subject's eye hereinafter). Ophthalmic observation is conducted to grasp the condition of the subject's eye in various situations such as examination, surgery, and treatment.

Conventional ophthalmic observation apparatuses are configured to provide a user with a magnified image formed by an objective lens, a variable magnification optical system, etc. via an eyepiece. In recent years, some ophthalmic observation apparatuses are configured to photograph a magnified image formed by an objective lens, a variable magnification optical system, etc. with an image sensor, and display the photographed image obtained (such an ophthalmic observation apparatus will be referred to as a digital ophthalmic observation apparatus). Examples of such digital ophthalmic observation apparatuses include surgical microscopes, slit lamp microscopes, and fundus cameras (retinal cameras). In addition, various kinds of ophthalmic examination apparatuses such as refractometers, keratometers, tonometers, specular microscopes, wavefront analyzers, and microperimeters are also provided with the function of the digital ophthalmic observation apparatus. PATENT DOCUMENT 1 noted below discloses a surgical microscope that functions as a digital ophthalmic observation apparatus.

Generally, an ophthalmic observation apparatus is configured to provide an image of a subject's eye to a user (e.g., a health professional (health care practitioner, healthcare worker) such as a doctor). A typical digital ophthalmic observation apparatus is configured to perform photographing of a moving image using infrared light and/or visible light as illumination light, and real-time display of the moving image obtained by the moving image photography. The real-time moving image (video, movie, moving picture, etc.) provided in these ways is referred to as an observation image or a live image.

An ophthalmic observation apparatus is used for observing various sites (parts, tissues) of the subject's eye. For example, while anterior eye segment observation can be performed with a standard optical system configuration, posterior eye segment observation requires optical elements different from those for anterior eye segment observation because of the need for guiding the illumination light to the posterior eye segment through the pupil and also guiding return light from the posterior eye segment to the optical system through the pupil. PATENT DOCUMENT 2 and PATENT DOCUMENT 3 disclose surgical microscopes configured to be able to switch observation modes between anterior eye segment observation and posterior eye segment observation by the non-use of or use of a front lens.

PATENT DOCUMENT 1: Japanese Unexamined Patent Application Publication No. 2019-162336

PATENT DOCUMENT 2: Japanese Unexamined Patent Application Publication No. 2019-013803

PATENT DOCUMENT 3: Japanese Unexamined Patent Application Publication No. 2019-092844

Widely used digital ophthalmic observation apparatus are configured in such a manner that the fundus of the subject's eye and an image sensor become optically conjugate with one another if the diopter of the subject's eye is normal (the subject's eye is emmetropic or correctly-focused eye) when an optical system configuration is changed to shift from anterior eye segment observation to posterior eye segment observation. However, since the majority of eyes have refractive errors (e.g., myopia, hyperopia, etc.) and there are individual differences in diopter, the eye fundus and the image sensor often do not form a conjugate relationship when the optical system configuration for posterior eye segment observation is selected. This makes it impossible for a digital ophthalmic observation apparatus to have the eye fundus in focus. Therefore, with conventional digital ophthalmic observation apparatuses, focus adjustment must be performed again after the shift to the optical system configuration for posterior eye segment observation. However, in the present circumstances, such a re-focus adjustment operation is omitted by introducing an additional concave lens and/or an additional convex lens. Even in this case, a fine adjustment operation of focus must be carried out at the end of the process. It should be noted that, as is well known in this technical field, situations in which such focus adjustment operations and/or fine adjustment operations of focus are/is required are not limited to the cases of shifting from anterior eye segment observation to posterior eye segment observation.

BRIEF SUMMARY

One object of the present disclosure is to provide a novel technique of focus adjustment in a digital ophthalmic observation apparatus.

An ophthalmic observation apparatus of some aspect examples includes: an illumination system that includes a light source configured to emit illumination light and an indicator member having a plurality of indicators and is configured to project the illumination light onto a subject's eye via the indicator member; a photography system that includes an image sensor and is configured to perform photography of the subject's eye; and a focus processor configured to perform detection of a plurality of indicator images from an image acquired by the photography system and perform a focus control of the photography system based on the plurality of indicator images.

In the ophthalmic observation apparatus of some aspect examples, the plurality of indicators may include two indicators arranged at positions away from an observation plane by optical distances different from each other.

In the ophthalmic observation apparatus of some aspect examples, one of the two indicators may be arranged on a side of the light source with respect to a position optically conjugate with the observation plane, and the other of the two indicators may be arranged on a side of the subject's eye with respect to the position optically conjugate with the observation plane.

In the ophthalmic observation apparatus of some aspect examples, at least one of the plurality of indicators may be arranged off an optical axis of the illumination system.

In the ophthalmic observation apparatus of some aspect examples, the plurality of indicators may include at least two indicators that have a same distance from the optical axis.

In the ophthalmic observation apparatus of some aspect examples, the at least two indicators may include two indicators arranged at symmetric positions with respect to the optical axis in a direction perpendicular to the optical axis.

In the ophthalmic observation apparatus of some aspect examples, at least two indicators of the plurality of indicators may be provided on a single member.

In the ophthalmic observation apparatus of some aspect examples, the single member may be a plane parallel plate through which the illumination light passes.

In the ophthalmic observation apparatus of some aspect examples, the plurality of indicators may include a first indicator provided on a first surface of the plane parallel plate and a second indicator provided on a second surface parallel to the first surface.

In the ophthalmic observation apparatus of some aspect examples, a position optically conjugate with an observation plane may be arranged between the first surface and the second surface.

In the ophthalmic observation apparatus of some aspect examples, the position optically conjugate with the observation plane may be arranged at a position that has a same distance from both the first surface and the second surface.

In the ophthalmic observation apparatus of some aspect examples, the focus processor may be configured to perform the focus control based on sizes of the plurality of indicator images.

In the ophthalmic observation apparatus of some aspect examples, the focus processor may be configured to perform a comparison between the sizes of the plurality of indicator images and perform the focus control based on a result of the comparison.

The ophthalmic observation apparatus of some aspect examples may further include: an objective lens; and a first movement mechanism configured to move the illumination system and the photography system in a direction along an optical axis of the objective lens. In addition, the focus processor may be configured to perform generation of movement control information that includes at least one of a movement direction and a movement distance based on the result of the comparison and then perform a control of the first movement mechanism based on the movement control information.

In the ophthalmic observation apparatus of some aspect examples, the plurality of indicators may include a pair of indicators of a same size that are arranged at two positions respectively. Here, the two positions are away from a position optically conjugate with an observation plane by a same optical distance in mutually opposite directions in a direction along the optical axis of the illumination system. In addition, the focus processor may be configured to perform the focus control in such a manner as to equalize sizes of two indicator images corresponding to the pair of indicators.

In the ophthalmic observation apparatus of some aspect examples, the focus processor may be configured to perform the focus control based on blurring of the plurality of indicator images.

The ophthalmic observation apparatus of some aspect examples may further include: an objective lens; a second movement mechanism configured to move the illumination system and the photography system in a direction perpendicular to an optical axis of the objective lens; an abnormal image detecting processor configured to perform image analysis to detect an abnormal image from the image acquired by the photography system; and a movement processor configured to perform a control of the second movement mechanism based on the abnormal image when the abnormal image is detected by the abnormal image detecting processor.

The ophthalmic observation apparatus of some aspect examples may further include: a cropping processor configured to perform cropping of a region of a predetermined size from the image acquired by the photography system; and an abnormal image detecting processor configured to perform image analysis to perform detection of an abnormal image from a partial image obtained by the cropping from the image. In addition, the cropping processor may be configured to move the region of the predetermined size to a region in the image that does not include the abnormal image when the abnormal image is detected by the abnormal image detecting processor.

The ophthalmic observation apparatus of some aspect examples may further include a mode switching unit configured to perform switching between a first observation mode for observing a first site of the subject's eye and a second observation mode for observing a second site that is different from the first site. In addition, the focus processor may be configured to perform the detection of the plurality of indicator images and the focus control in response to performance of observation mode switching by the mode switching unit.

In the ophthalmic observation apparatus of some aspect examples, the first observation mode may be an anterior eye segment observation mode for observing an anterior eye segment of the subject's eye, and the second observation mode may be a posterior eye segment observation mode for observing a posterior eye segment of the subject's eye. In addition, the mode switching unit may include a lens that is inserted into an optical path in order to switch from the anterior eye segment observation mode to the posterior eye segment observation mode.

These aspect examples allow a novel technique of focus adjustment in a digital ophthalmic observation apparatus to be provided.

DETAILED DESCRIPTION

Figure 1:
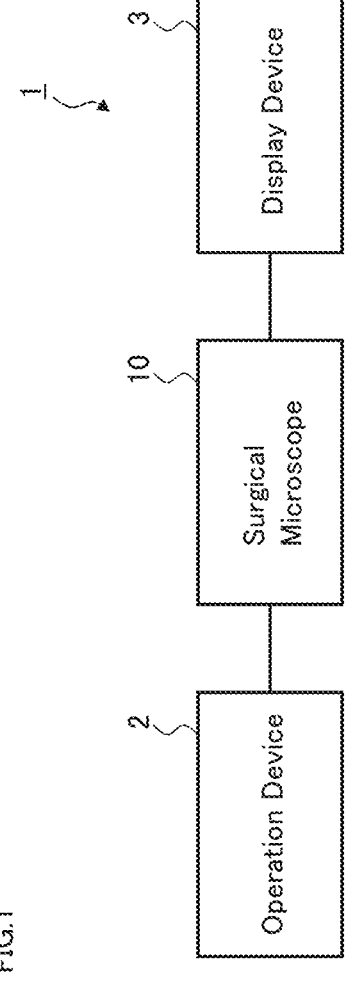
FIG. 1 is a diagram illustrating an example of a configuration of an ophthalmic observation apparatus (surgical microscope system, operation microscope system) according to an embodiment example.

Several aspect examples of an ophthalmic observation apparatus according to embodiment examples will be described in detail with reference to the drawings of the present disclosure. It should be noted that any of the matters and items described in the documents cited in the present disclosure and any known techniques and technologies may be combined with any of the aspect examples.

The ophthalmic observation apparatus according to some aspect examples is used in medical practice (healthcare practice) such as surgery, examination, and treatment of the subject's eye, in order to grasp (understand, recognize, find) the state of the subject's eye. The ophthalmic observation apparatus of the aspect examples described herein is mainly a surgical microscope system. However, ophthalmic observation apparatuses of embodiments are not limited to surgical microscope systems. For example, the ophthalmic observation apparatus of some aspect examples may be any of a slit lamp microscope, a fundus camera, a refractometer, a keratometer, a tonometer, a specular microscope, a wavefront analyzer, and a microperimeter. Also, the ophthalmic observation apparatus of some aspect examples may be a system that includes any one or more of these apparatus examples. In a wider sense, the ophthalmic observation apparatus of some aspect examples may be any type of ophthalmic apparatus having an observation function.

A target ocular site for observation (ocular site to be observed, ocular site subject to observation) by using the ophthalmic observation apparatus may be any site of the subject's eye, and may be any site of the anterior segment and/or any site of the posterior segment. Examples of the observation target sites of the anterior segment include cornea, iris, anterior chamber, corner angle, crystalline lens, ciliary body, and zonule of Zinn. Examples of the observation target sites of the posterior segment include retina, choroid, sclera, and vitreous body. The observation target site is not limited to tissues of an eye ball, and may be any site subject to be observed in ophthalmic medical practice (and/or medical practice in other medical fields) such as eyelid, meibomian gland, and orbit (eye socket, eye pit).

At least one or more of the functions of the elements described in the present disclosure are implemented by using a circuit configuration (or circuitry) or a processing circuit configuration (or processing circuitry). The circuitry or the processing circuitry includes any of the followings, all of which are configured and/or programmed to execute at least one or more functions disclosed herein: a general purpose processor, a dedicated processor, an integrated circuit, a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), a conventional circuit configuration or circuitry, and any combination of these. A processor is considered to be processing circuitry or circuitry that includes a transistor and/or another circuitry. In the present disclosure, circuitry, a unit, a means, or a term similar to these is hardware that executes at least one or more functions disclosed herein, or hardware that is programmed to execute at least one or more functions disclosed herein. Hardware may be the hardware disclosed herein, or alternatively, known hardware that is programmed and/or configured to execute at least one or more functions described herein. In the case where the hardware is a processor, which may be considered as a certain type of circuitry, then circuitry, a unit, a means, or a term similar to these is a combination of hardware and software. In this case, the software is used to configure the hardware and/or the processor.

<Ophthalmic Observation Apparatus>

FIG. 1 shows the configuration of the ophthalmic observation apparatus of some aspect examples.

The ophthalmic observation apparatus 1 (surgical microscope system, operation microscope system) according to the present embodiment includes the operation device 2, the display device 3, and the surgical microscope (operation microscope) 10. In some aspect examples, the surgical microscope 10 may include at least one of the operation device 2 and the display device 3. In some aspect examples, the display device 3 may not be included in the ophthalmic observation apparatus 1. In other words, the display device 3 may be a peripheral device of the ophthalmic observation apparatus 1.

<Operation Device 2>

The operation device 2 includes an operation device and/or an input device. For example, the operation device 2 may include any of a button, a switch, a mouse, a keyboard, a trackball, an operation panel, a dial, and the like. Typically, the operation device 2 includes a foot switch, like standard (general, normal, usual) ophthalmic surgical microscopes. Further, the operation device 2 may also be configured in such a manner that the user performs operations using voice recognition, line-of-sight (gaze) input, or like input technologies.

<Display Device 3>

The display device 3 displays an image of the subject's eye acquired by the surgical microscope 10. The display device 3 includes a display device such as a flat panel display. The display device 3 may include any of various kinds of display devices such as a touch panel. The display device 3 of some typical aspects includes a display device with a large screen. The display device 3 includes one or more display devices. In the case where the display device 3 includes two or more display devices, for example, one may be a display device with a relatively large screen and one of the other(s) may be a display device with a relatively small screen. Also, a configuration may be employed in which a plurality of display regions is provided in one display device to display a plurality of pieces of information.

The operation device 2 and the display device 3 do not have to be separate devices. For example, a device having both the operation function and the display function, such as a touch panel, may be used as the display device 3. In such a case, the operation device 2 may include a computer program in addition to the touch panel. A content of an operation made by the operation device 2 is sent to a processor (not shown in the drawings of the present disclosure) as an electric signal. Further, a graphical user interface (GUI) displayed on the display device 3 and the operation device 2 may be used to conduct operations (instructions) and input information. In some aspect examples, the functions of the operation device 2 and the display device 3 may be implemented with a touch screen.

<Surgical Microscope 10>

The surgical microscope 10 is used for observation of the eye of a patient (subject's eye) in the supine position. The surgical microscope 10 performs photographing of the subject's eye to generate digital image data (moving image data). In particular, the surgical microscope 10 generates a moving image (video, movie) of the subject's eye. The moving image generated by the surgical microscope is transmitted to the display device 3 through a wired and/or wireless signal path and displayed on the display device 3. The user (e.g., surgeon) can carry out surgery while observing the subject's eye through the displayed image (observation image, live image). In addition to such an observation mode through the moving image, the surgical microscope 10 of some aspect examples may be capable of providing observation through an eyepiece as in the past.

In some aspect examples, the surgical microscope 10 includes a communication device for transmitting and receiving electrical signals to and from the operation device 2. The operation device 2 receives an operation (instruction) performed by the user and generates an electric signal (operation signal) corresponding to the operation. The operation signal is transmitted to the surgical microscope 10 through a wired and/or wireless signal path. The surgical microscope executes processing corresponding to the operation signal received.

Observation modes executed by using the surgical microscope 10 of the present aspect include an anterior eye segment observation mode and a posterior eye segment observation mode. The anterior eye segment observation mode is used to observe enlarged images of various sites of the anterior eye segment such as the cornea Ec. The posterior eye segment observation mode is used to observe images of various sites of the posterior eye segment such as the fundus Ef. A front lens (the front lens 21 described later) is used to perform the posterior eye segment observation mode. When the front lens 21 is place in the optical path, the combination of the objective lens 20 and the front lens 21 can be considered as an objective lens.

An example of the configuration of the optical system of the surgical microscope 10 will be described. Below, directions are defined as follows, for convenience of description: the Z direction is defined to be the optical axis direction (direction along the optical axis) of the objective lens (the Z direction is, for example, the vertical direction, the up and down direction during surgery); the X direction is defined to be a predetermined direction perpendicular to the Z direction (the X direction is, for example, the horizontal direction during surgery, and the left and right direction for the surgeon and the patient during surgery); and the Y direction is defined to be the direction perpendicular to both the Z and X directions (the Y direction is, for example, the horizontal direction during surgery, the front and back direction for the surgeon during surgery, and the body axis direction (direction along the body axis) for the patient during surgery).

The observation optical system of the surgical microscope 10 includes a pair of optical systems. One of the optical systems acquires moving image data presented to the user's left eye, and the other of the optical systems acquires moving image data presented to the right eye. This allows the user to conduct observation with both eyes (binocular observation), particularly stereoscopic viewing (stereoscopic observation).

Figure 2:
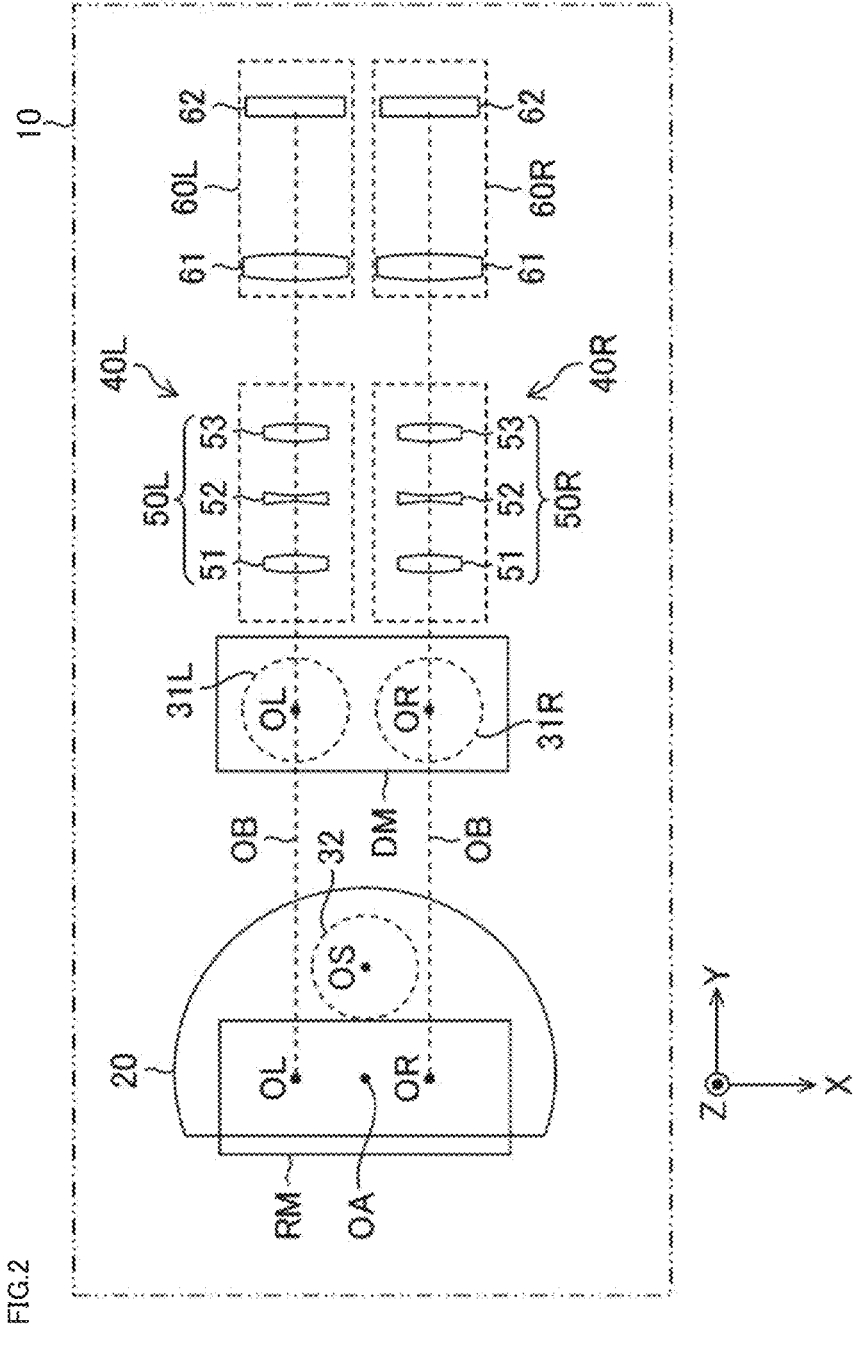
FIG. 2 is a diagram illustrating an example of a configuration of an ophthalmic observation apparatus according to an embodiment example.
Figure 3:
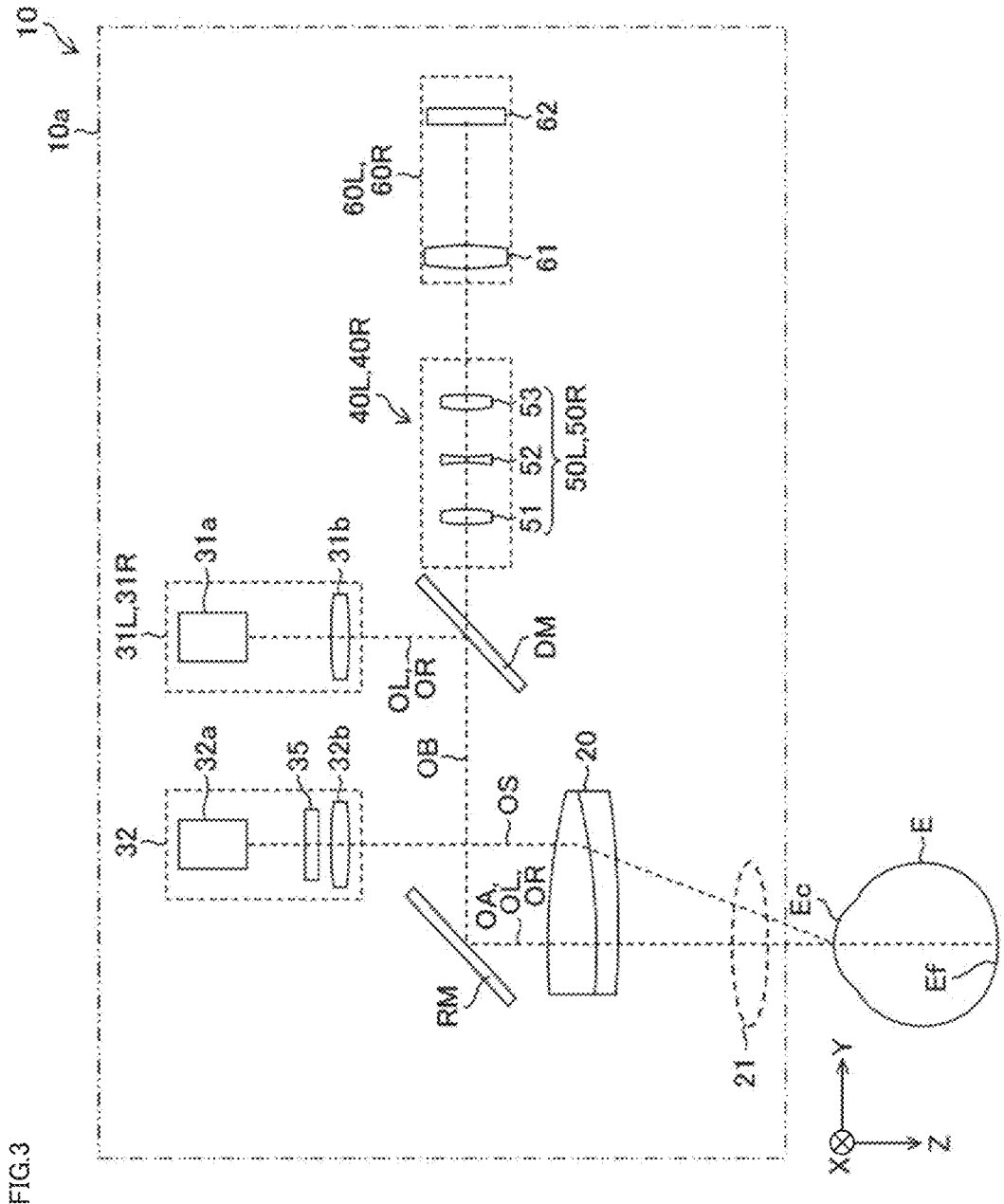
FIG. 3 is a diagram illustrating an example of a configuration of an ophthalmic observation apparatus according to an embodiment example.

FIG. 2 and FIG. 3 show examples of the configuration of the optical system of the surgical microscope 10. FIG. 2 is a schematic diagram of the optical system viewed from a position on the subject's eye E side, and FIG. 3 is a schematic diagram of the optical system viewed from the side. In order to simplify the illustration, the illumination optical system 30 arranged above the objective lens 20 is omitted in FIG. 2.

The surgical microscope 10 includes the objective lens 20, the reflection mirror RM, the dichroic mirror DM, the illumination optical system 30, and the observation optical system 40. In addition, the surgical microscope 10 includes the front lens 21 for use in the posterior eye segment observation mode. The observation optical system 40 includes the zoom expander 50, and the imaging camera 60. In some aspect examples, the illumination optical system 30 (the first illumination optical systems 31L and 31R) and/or the observation optical system 40 includes the reflection mirror RM. Also, in some aspect examples, the illumination optical system 30 (the first illumination optical systems 31L and 31R) and/or the observation optical system 40 includes the dichroic mirror DM.

The objective lens 20 is arranged to face the subject's eye E. The optical axis OA of the objective lens 20 is arranged (oriented) parallel to the Z direction. The objective lens 20 may include two or more lenses.

The dichroic mirror DM couples the optical path of the illumination optical system 30 (the first illumination optical systems 31L and 31R) and the optical path of the observation optical system 40 with each other. The dichroic mirror DM is arranged between the zoom expander 50 and the reflection mirror RM. The dichroic mirror DM reflects illumination light from the illumination optical system 30 (the first illumination optical systems 31L and 31R) and directs the illumination light to the subject's eye E through the reflection mirror RM and the objective lens 20 (and the front lens 21). Also, the dichroic mirror DM transmits return light from the subject's eye E guided by (the front lens 21 and) the objective lens 20 and the reflection mirror RM and directs the return light to the imaging camera 60 through the zoom expander 50.

The dichroic mirror DM coaxially couples the optical path of the illumination optical system 30 (the first illumination optical systems 31L and 31R) and the optical path of the observation optical system 40 with each other. In other words, the optical axis of the illumination optical system 30 and the optical axis of the observation optical system 40 intersect at the dichroic mirror DM. In the present aspect, the illumination optical system 30 includes an illumination optical system for left eye (31L) and an illumination optical system for right eye (31R), and the observation optical system 40 includes an observation optical system for left eye 40L and an observation optical system for right eye 40R. The dichroic mirror DM coaxially couples the optical path of the illumination optical system for left eye (the first illumination optical system 31L) and the optical path of the observation optical system for left eye 40L with each other, and coaxially couples the optical path of the illumination optical system for right eye (the first illumination optical system 31R) and the optical path of the observation optical system for right eye 40R with each other. In other words, the optical axis OL of the illumination optical system for left eye (the first illumination optical system 31L) and the optical axis OB of the observation optical system for left eye 40L intersect at the dichroic mirror DM, and the optical axis OR of the illumination optical system for right eye (the first illumination optical system 31R) and the optical axis OB of the observation optical system for right eye 40R intersect at the dichroic mirror DM.

The reflection mirror RM is arranged above the objective lens 20. The upper end of the optical axis OA of the objective lens 20 extending in the Z direction is located on the reflection mirror RM. Also, the reflection mirror RM deflects the optical axis OB of the observation optical system 40L extending in the Y direction and the optical axis OB of the observation optical system 40R extending in the Y direction in such a manner that these optical axes OB become parallel to the optical axis OA of the objective lens 20 (in such a manner that these optical axes OB become oriented along the Z direction). The optical axis OA of the objective lens 20 is located in the middle position between the optical axis OB of the observation optical system and the optical axis OB of the observation optical axis 40R on the reflection mirror RM. The first illumination optical systems 31L and 31R are provided above the dichroic mirror DM. The second illumination optical system 32 is provided above the objective lens 20. The second illumination optical system 32 is arranged at a position shifted toward the dichroic mirror DM with respect to the reflection mirror RM. In other words, the optical axis OS of the second illumination optical system 32 is located closer to the dichroic mirror DM than the optical axis OA of the objective lens 20 is to the dichroic mirror DM.

The illumination optical system 30 is an optical system for illuminating the subject's eye E through the objective lens 20 (and the front lens 21). The illumination optical system 30 may be configured to selectively illuminate the subject's eye E with two or more kinds of illumination light having different color temperatures. The illumination optical system 30 projects illumination light having a designated color temperature onto the subject's eye E under the control of a controller (the controller 200 described later).

As mentioned above, the illumination optical system 30 includes the first illumination optical systems 31L and 31R and the second illumination optical system 32.

The illumination method using the first illumination optical systems 31L and 31R is referred to as "coaxial illumination", which makes it possible to generate a red reflex image (transillumination image) formed by utilizing diffuse reflection from eye fundus. In the present aspect, the user can observe the red reflex image of the subject's eye E with both eyes. In other words, in the present aspect, it is possible to photograph the red reflex image of the subject's eye E with both the observation optical system for left eye 40L and the observation optical system for right eye 40R, and to display a pair of red reflex images obtained.

The optical axis OS of the second illumination optical system 32 is arranged at a position shifted from the optical axis OA of the objective lens 20 in the Y direction. The first illumination optical systems 31L and 31R and the second illumination optical system 32 are arranged in such a manner that the deviation of the optical axis OS with respect to the optical axis OA of the objective lens 20 is larger than the deviations of the optical axes OL and OR with respect to the optical axis OA of the objective lens 20. Such arrangements enable an illumination mode referred to as "angled illumination (oblique illumination, tilted illumination)" and therefore enables binocular observation of the subject's eye E while preventing ghosting caused by corneal reflection or the like. In addition, the arrangements enable detailed observation of unevenness and irregularities of sites and tissues of the subject's eye E.

The first illumination optical system 31L includes the light source 31a and the condenser lens 31b. The light source 31a outputs illumination light having a wavelength in the visible range (visible region) corresponding to color temperature of 3000 K (kelvins), for example. The illumination light emitted from the light source 31a passes through the condenser lens 31b, is reflected by the dichroic mirror DM, is reflected by the reflection mirror RM, passes through the objective lens 20 (and the front lens 21), and then is incident on the subject's eye E. The same applies to the first illumination optical system 31R.

The second illumination optical system 32 includes the light source 32a, the lens 32b, and the indicator member 35. The indicator member 35 is arranged between the light source 32a and the lens 32b. The light source 32a may include a condenser lens which is not shown in the drawings of the present disclosure. The light source 32a outputs illumination light having a wavelength in the visible range corresponding to a color temperature within the range of 4000 K to 6000 K, for example. The indicator member 35 is provided with a plurality of indicators. The details of this plurality of indicators will be described later. The lens 32b has a function of projecting the plurality of indicators provided on the indicator member 35 onto the subject's eye E.

The indicator member 35 provides a plurality of indicators that can be used for focus adjustment (focus control) of the observation optical system 40 with respect to the subject's eye E. The indicator member 35 may have a freely designed configuration and may include a freely selected or determined device and/or element. For example, the indicator member 35 may include any one or more of the following devices and elements: one or more optical elements, such as a translucent plate-like member (typically a plane parallel plate), provided with a reticle (e.g., cross indicator, pinhole indicator) as an indicator; one or more diaphragm members whose apertures can be used as indicators; a plurality of light sources (e.g., a plurality of light emitting elements such as LEDs); and a light transmissive display (e.g., light transmissive LCD, light transmissive OLED).

The illumination light output from the light source 32a passes through the indicator member 35 and the lens 32b, is refracted by the objective lens 20 (and the front lens 21) without passing through the reflection mirror RM, and is incident on the subject's eye E.

The arrangement and aspects of the plurality of indicators provided in the indicator member 35 may be freely designed. Also, it may be possible to change the arrangement and/or aspects of the plurality of indicators. The aspects (shapes, sizes, dimensions, colors, etc.) of the plurality of indicators may be the same or may be individually different. Several examples of the arrangement of the plurality of indicators are described below. It should be noted that at least two of these examples can be combined together at least in part.

The first example of the arrangement of the plurality of indicators will be described. The present example pays attention to the optical distance from the observation plane. The plurality of indicators of the present example at least includes two indicators with individually different optical distances from the observation plane. The observation plane is, so to speak, the position that the user wants to have in focus the most (that is, the position (site, depth) that the user focuses on when observing the subject's eye E), and is the position (observation position) that the user wants to form an optically conjugate relationship with respect to the image sensor 62 of the observation optical system 40.

In the case where the subject's eye E is a correctly-focused eye, if this optically conjugate relationship is achieved in the anterior eye segment observation mode, then it becomes the case that a desired observation plane of the posterior eye segment (typically, the fundus Ef (retina)) is still in focus after the observation mode is shifted to the posterior eye segment observation mode by inserting the front lens 21 into the optical path. Therefore, it can be said that focus adjustment is almost unnecessary even if the observation site is changed.

In contrast, in the case where the subject's eye E has a refractive error, a desired observation plane of the posterior eye segment becomes out of focus when the observation mode is shifted to the posterior eye segment observation mode even if a preferable optically conjugate relationship is achieved in the anterior eye segment observation mode. Therefore, by projecting the two indicators according to the present specific example and conducting photography, two indicator images that have individually different focus states (focus conditions) are depicted in the photographed image. As a result of this, the current focus state of the observation optical system 40 can be understood from a specific parameter (e.g., size, dimension, blurring) related to these indicator images, and therefore focus adjustment can be performed (details thereof are described below).

A specific example of the first example will be described. In this specific example, a plane conjugate with the observation plane is placed between the two indicators. In other words, one indicator is disposed on the side of the light source 32a with respect to a plane optically conjugate with the observation plane (a plane intersecting the optical path of the second illumination optical system 32), and the other indicator is disposed on the side of the lens 32b (the side of the subject's eye E) with respect to the plane optically conjugate with the observation plane. By referring to two indicator images corresponding to such two indicators, it becomes possible to understand the focus state and perform focus adjustment.

The second example of arrangement of the plurality of indicators will be described. At least one of the plurality of indicators in the present example is disposed at a position out of the optical axis OS of the second illumination optical system 32. In other words, at least one of the plurality of indicators in the present example is arranged at a position off the optical axis OS of the second illumination optical system 32. If two (or more) indicators were both (all) placed on the optical axis OS, their images would overlap in a photographed image, making them indistinguishable, and therefore making the indicators meaningless. One of the aims of the present example is to avoid such a problem by arranging two (or more) indicators at individually different positions in the direction perpendicular to the optical axis OS (that is, in the XY direction).

A specific example of the second example will be described. In this specific example, the plurality of indicators includes at least two indicators that have the same distance from the optical axis OS of the second illumination optical system 32. In other words, when projecting the three dimensional coordinates (XYZ coordinates) of each of the at least two indicators onto the XY plane which is perpendicular to the optical axis OS, the at least two projection positions (XY coordinates) corresponding to the at least two indicators exist on the same circle centered around the XY coordinates of the axis OS.

For example, the at least two indicators with the same distance from the optical axis OS include two indicators arranged at symmetric positions with respect to the optical axis OS in a direction perpendicular to the optical axis OS (that is, in the XY direction). In other words, when projecting the XYZ coordinates of each of the two indicators onto the XY plane, the two XY coordinates corresponding to the two indicators exist at point-symmetric positions with respect to the XY coordinates of the optical axis OS.

Such a regular arrangement of the plurality of indicators can facilitate and expedite processing because an area to be analyzed can be narrowed down in detecting an indicator image (see below), compared to the case where the plurality of indicators is arranged irregularly. In addition, when manually performing a fine focus adjustment operation while referring to a displayed image in which indicator images are depicted, the user becomes able to easily find the indicator images, and further becomes able to easily perform a comparison between the indicator images.

The third example of arrangement of the plurality of indicators will be described. In the present example, at least two indicators of the plurality of indicators are provided on a single member. This single member is included in the indicator member 35. In typical examples, the indicator member 35 consists of one or more members. According to the present example, the configuration of the indicator member 35 can be simplified compared to the case, for example, in which two indicators are provided in different members. It should be noted that the indicator member 35 may be composed of two or more members to which the plurality of indicators has been distributed (that is, two or more members each of which has at least one of the plurality of indicators).

A specific example of the third example will be described. The aforementioned single member of the present specific example is a plane parallel plate configured to transmit the illumination light output from the light source 32a. The plurality of indicators may include the first indicator provided on the first surface of the plane parallel plate and the second indicator provided on the second surface parallel to the first surface. In other words, the plane parallel plate may be configured in such a manner that an indicator is provided on each of the two surfaces parallel to each other. These two surfaces are referred to as both surfaces. Furthermore, a position conjugate with the observation plane may be arranged between the both surfaces of the plane parallel plate. To put it differently, it may be configured that the position conjugate with the observation plane is inside the plane parallel plate. In addition, the position conjugate with the observation plane may be arranged on the center plane of the plane parallel plate. In other words, it may be configured that the position optically conjugate with the observation plane is arranged at a position that has the same distance from the both surfaces of the plane parallel plate. This specific example can provide a configuration example of the first example described above. Typically, in the case where the indicator member 35 includes a plate-like member such as a plane parallel plate, the arrangement state of the plate-like member with respect to the optical axis OS of the second illumination optical system 32 may be freely designed or determined. For example, a plane parallel plate may be oriented in such a manner that the two optical surfaces of the plane parallel plate are perpendicular to the optical axis OS or oblique (non-perpendicular and non-parallel) to the optical axis OS.

The color temperature of the illumination light from the first illumination optical systems 31L and 31R may be lower than the color temperature of the illumination light from the second illumination optical system 32. Such a configuration makes it possible to observe the subject's eye E in warm colors using the first illumination optical systems 31L and 31R, and therefore enables detailed observation of the structure and morphology of the subject's eye E.

In some aspect examples, each of the optical axes OL and OR is movable relative to the optical axis OA of the objective lens 20. The direction of the relative movement is a direction that intersects the optical axis OA of the objective lens 20, and the relative movement is represented by a displacement vector in which at least one of the X component and the Y component is not zero. In some aspect examples, the optical axes OL and OR may be mutually independently movable. On the other hand, in some aspect examples, the optical axes OL and OR may be integrally movable. For example, the surgical microscope 10 includes a movement mechanism (31d) configured to move the first illumination optical systems 31L and 31R mutually independently or integrally, and therefore the movement mechanism moves the first illumination optical systems 31L and 31R mutually independently or integrally in a direction intersecting the optical axis OA of the objective lens 20. Such a configuration makes it possible to conduct adjustment of the appearance condition (appearance state) of the subject's eye E. In some aspect examples, the movement mechanism operates under the control of a controller (the controller 200 described later).

In some aspect examples, the optical axis OS is movable relative to the optical axis OA of the objective lens 20. The direction of the relative movement is a direction that intersects the optical axis OA of the objective lens 20, and the relative movement is represented by a displacement vector in which at least one of the X component and the Y component is not zero. For example, the surgical microscope 10 includes a movement mechanism (32d) configured to move the second illumination optical system 32, and therefore the movement mechanism moves the second illumination optical system 32 in a direction that intersects the optical axis OA of the objective lens 20. With such a configuration, it becomes possible to conduct adjustment of the appearance condition (appearance state) of unevenness and irregularities of sites and tissues of the subject's eye E. In some aspect examples, the movement mechanism operates under the control of a controller (the controller 200 described later).

As described above, the present aspect is configured in such a manner as to project the illumination light onto the subject's eye E from the position directly above the objective lens 20 and in such a manner that the optical axis OB of the observation optical system 40 is oriented horizontally (along the Y direction). However, the arrangement of the optical system is not limited to that of the present aspect. For example, the observation optical system 40 may be arranged in such a manner that the angle formed by the optical axis OB of the observation optical system 40 and the plane perpendicular to the optical axis OA of the objective lens 20 (the XY plane) belongs to the range between −20 degrees and +20 degrees.

According to the configuration of the present aspect, the observation optical system 40, which typically has a longer optical path length than the illumination optical system 30, is arranged substantially parallel to the XY plane. Hence, the observation optical system 40 of the present aspect does not interfere with the surgeon's field of view while conventional surgical microscopes, whose observation optical system is oriented along the vertical direction in front of the surgeon's eyes, do. Therefore, the surgeon is capable of easily seeing the screen of the display device 3 arranged in front of the surgeon. In other words, the visibility of displayed information (images and videos of the subject's eye E, and other various kinds of reference information) during surgery etc. is improved. In addition, since the housing is not placed in front of the surgeon's eyes, it does not give a sense of oppression to the surgeon, thereby reducing the burden on the surgeon.

The observation optical system 40 is an optical system for observation of an image formed based on return light of the illumination light incident from the subject's eye E through (the front lens 21 and) the objective lens 20. In the present aspect, the observation optical system 40 guides the image to an image sensor of the imaging camera 60. The observation optical system 40 has a function as a photography system.

As described above, the observation optical system 40 includes the observation optical system for left eye 40L and the observation optical system for right eye 40R. The configuration of the observation optical system for left eye 40L and the configuration of the observation optical system for right eye 40R are the same as or similar to one another. In some aspect examples, the observation optical system for left eye 40L and the observation optical system for right eye 40R may be configured such that their optical arrangements can be changed independently of each other.

The zoom expander 50 is also referred to as a beam expander, a variable beam expander, or the like. The zoom expander 50 includes the zoom expander for left eye 50L and the zoom expander for right eye 50R. The configuration of the zoom expander for left eye 50L and the configuration of the zoom expander for right eye are the same as or similar to each other. In some aspect examples, the zoom expander for left eye 50L and the zoom expander for right eye 50R may be configured such that their optical arrangements can be changed independently of each other.

The zoom expander for left eye 50L includes the plurality of zoom lenses 51, 52, and 53. At least one of the zoom lenses 51, 52, and 53 is movable in the direction along the optical axis by means of a variable magnification mechanism (the variable magnification mechanism 50Ld described later).

Similarly, the zoom expander for right eye 50R includes the plurality of zoom lenses 51, 52, and 53, and at least one of the zoom lenses 51, 52, and 53 is movable in the direction along the optical axis by means of a variable magnification mechanism (the variable magnification mechanism 50Rd described later).

The variable magnification mechanism(s) may be configured to move a zoom lens of the zoom expander for left eye 50L and a zoom lens of the zoom expander for right eye 50R mutually independently or integrally in the directions along the optical axes. As a result of this, the magnification ratio for photographing the subject's eye E is changed. In some aspect examples, the variable magnification mechanism(s) operates under the control of a controller (the controller 200 described later).

The imaging camera 60 is a device that photographs an image formed by the observation optical system 40 and generates digital image data. The imaging camera 60 is typically a digital camera (digital video camera). The imaging camera includes the imaging camera for left eye 60L and the imaging camera for right eye 60R. The configuration of the imaging camera for left eye 60L and the configuration of the imaging camera for right eye 60R are the same as or similar to one another. In some aspect examples, the imaging camera for left eye 60L and the imaging camera for right eye 60R may be configured such that their optical arrangements can be changed independently of each other.

The imaging camera for left eye 60L includes the imaging lens 61 and the image sensor 62. The imaging lens 61 forms an image based on the return light that has passed through the zoom expander for left eye 50L, on the imaging surface (light receiving surface) of the image sensor 62. The image sensor 62 is an area sensor, and may typically be a charge-coupled device (CCD) image sensor or a complementary metal oxide semiconductor (CMOS) image sensor. The image sensor 62 operates under the control of a controller (the controller 200 described later).

The imaging camera for right eye 60R includes the imaging lens 61 and the image sensor 62. The imaging lens 61 forms an image based on the return light that has passed through the zoom expander for right eye 50R, on the imaging surface (light receiving surface) of the image sensor 62. The image sensor 62 is an area sensor, and may typically be a CCD image sensor or a CMOS image sensor. The image sensor 62 operates under the control of a controller (the controller 200 described later).

<Processing System>

Figure 4:
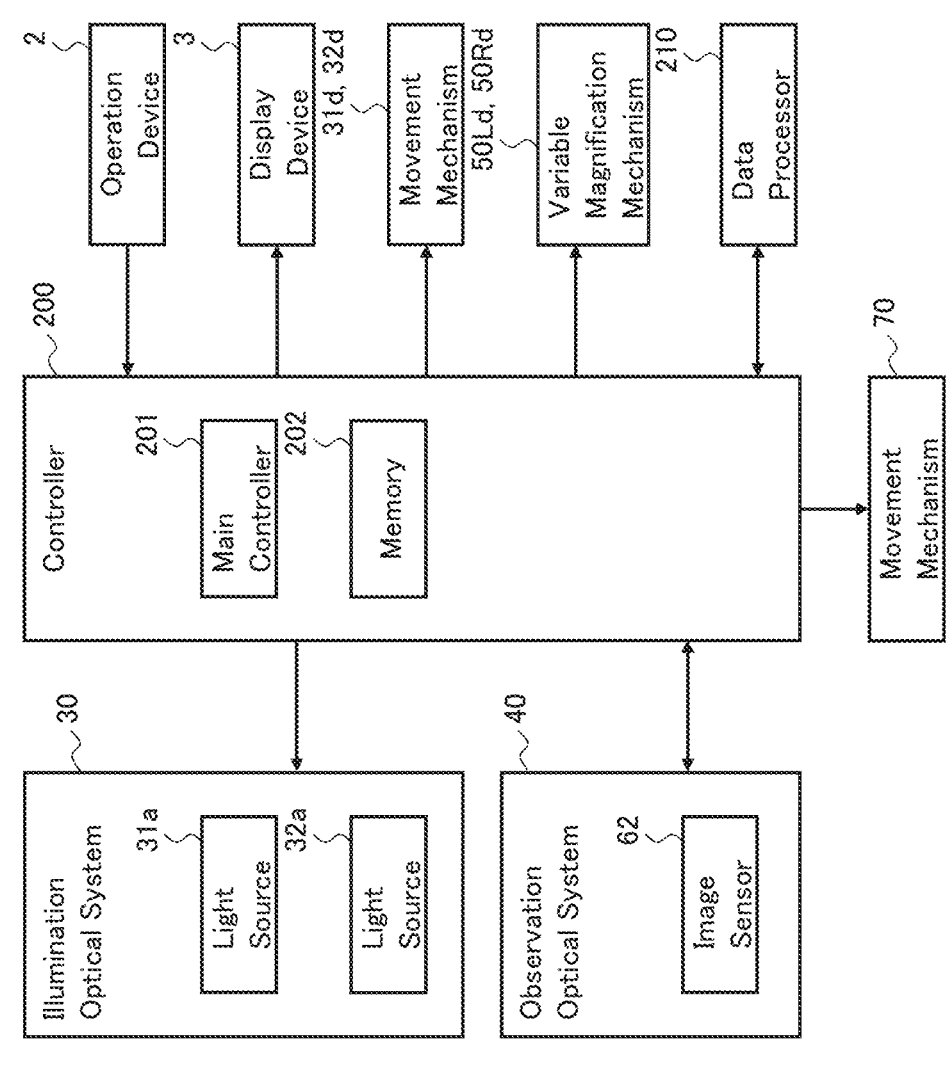
FIG. 4 is a diagram illustrating an example of a configuration of an ophthalmic observation apparatus according to an embodiment example.

Several examples of the processing system of the ophthalmic observation apparatus 1 will be described with reference to FIG. 4. Any two or more of the various kinds of configuration examples described below may be combined at least in part.

The controller 200 executes a control of each part of the ophthalmic observation apparatus 1. The controller 200 includes the main controller 201 and the memory 202. The main controller 201 includes a processor and executes a control of each part of the ophthalmic observation apparatus 1. For example, the processor may load and run a program stored in the memory 202 or another storage device, thereby implementing a function according to the present aspect. In addition, the processor may use (e.g., referring, processing, calculating, etc.) data and/or information stored in the memory 202 or another storage device in order to implement a function according to the present aspect.

The main controller 201 may execute the following controls: a control of each of the two light sources 31a of the illumination optical system 30; a control of the light source 32a of the illumination optical system 30; a control of each of the two image sensors 62 of the observation optical system 40; a control of each of the movement mechanisms 31d and 32d; a control of each of the variable magnification mechanisms 50Ld and 50Rd; a control of the operation device 2; a control of the display device 3; and a control of other component parts.

Controls of the light source 31a include turning on and off the light source, adjusting the light amount, adjusting the illumination diaphragm (aperture), and so forth. Controls of the light source 32a include turning on and off the light source, adjusting the light amount, adjusting the illumination diaphragm (aperture), and so forth. In the case where the illumination optical system 30 includes a light source whose color temperature can be varied, the main controller 201 may change the color temperature of emitted illumination light by controlling such a light source.

Controls of the image sensor 62 include exposure adjustment, gain adjustment, photographing rate adjustment, and so forth. The main controller 201 may control the two image sensors 62 in such a manner that the photographing timings of the two image sensors 62 match each other, or control the two image sensors 62 in such a manner that the difference between the photographing timings of the two image sensors 62 lies within a predetermined time. In addition, the main controller 201 may perform a control of loading digital data obtained by each of the image sensors 62.

The movement mechanism 31d moves the two light sources 31a mutually independently or integrally in a direction that intersects the optical axis of the objective lens 20. By controlling the movement mechanism 31d, the main controller 201 moves the optical axes OL and OR of the illumination optical system 30 mutually independently or integrally with respect to the optical axis OA of the objective lens 20.

The movement mechanism 32d moves the light source 32a in a direction that intersects the optical axis of the objective lens 20. By controlling the movement mechanism 32d, the main controller 201 moves the optical axis OS with respect to the optical axis OA of the objective lens 20.

The movement mechanism 70 moves the surgical microscope 10. For example, the movement mechanism 70 is configured to integrally move at least part of the illumination optical system 30 and the observation optical system 40. This configuration makes it possible to change the relative positions of the at least part of the illumination optical system 30 and the observation optical system 40 with respect to the subject's eye E while maintaining the relative positional relationship between at least part of the illumination optical system 30 and the observation optical system 40. In some aspect examples, the movement mechanism 70 is configured to integrally move the first illumination optical systems 31L and 31R and the observation optical system 40. With this, the relative positions of the first illumination optical systems 31L and 31R with respect to the subject's eye E and the relative position of the observation optical system 40 with respect to the subject's eye E can be changed while maintaining the state (condition) of coaxial illumination. In some aspect examples, the movement mechanism 70 is configured to integrally move the second illumination optical system 32 and the observation optical system 40. With this, the relative positions of the second illumination optical system 32 and the observation optical system 40 with respect to the subject's eye E can be changed while maintaining the illumination angle for oblique illumination. In some aspect examples, the movement mechanism 70 is configured to integrally move the first illumination optical systems 31L and 31R, the second illumination optical system 32, and the observation optical system 40. This makes it possible to change the relative positions of the illumination optical system 30 and the observation optical system 40 with respect to the subject's eye E while maintaining both the state (condition) of coaxial illumination and the illumination angle for oblique illumination.

The movement mechanism 70 may be configured to move the surgical microscope 10 in a freely determined direction. For example, the movement mechanism 70 may be configured to be capable of moving the surgical microscope 10 in three dimensional manner. In other words, the movement mechanism 70 may be capable of moving the surgical microscope 10 in each of the X, Y, and Z directions, and may also be capable of moving the surgical microscope 10 in any direction defined as a combination of at least two of the X, Y, and Z directions.

Movements in the XY direction (e.g., movements in the X direction, movements in the Y direction, movements in a combined direction of the X direction and the Y direction)

are performed in various aspects or modes of moving the illumination optical system 30 and the observation optical system 40 together as described above. A group of elements of the movement mechanism 70 for moving the surgical microscope 10 in the XY direction corresponds to the second movement mechanism.

Movements in the Z direction is performed for conducting focus adjustment of the observation optical system 40. By moving the observation optical system 40 in the Z direction, the focal point of the observation optical system 40 is moved in the Z direction. A group of elements of the movement mechanism 70 for moving the surgical microscope 10 in the Z direction corresponds to the first movement mechanism. Note that the method or technique for focus adjustment of the observation optical system 40 is not limited to this aspect example. Like a fundus camera, an observation optical system (photography system) of some aspect examples may include a focus lens and a mechanism that moves the focus lens.

Further, the ophthalmic observation apparatus 1 may be configured to perform focus adjustment by moving the front lens 21 when the front lens 21 is placed in the optical path, and to perform focus adjustment by moving the objective lens 20 when the front lens 21 is not placed in the optical path.

In a wider sense, the ophthalmic observation apparatus 1 may be configured to perform focus adjustment by any one of the following actions or a combination of any two or more of the following actions: a movement of at least one or more of the elements of the illumination optical system 30; a movement of at least one or more of the elements of the observation optical system 40; a movement of the objective lens 20; and a movement of the front lens 21.

The movement mechanism 70 operates under a control of the controller 200.

In some aspect examples, the main controller 201 may be configured to control at least two of the movement mechanisms 31d, 32d, and 70 in an interlocking manner.

The variable magnification mechanism 50Ld moves at least one of the plurality of zoom lenses 51 to 53 of the zoom expander for left eye 50L in the optical axis direction (direction along the optical axis). The main controller 201 changes the magnification ratio of the observation optical system for left eye 40L by controlling the variable magnification mechanism 50Ld.

Similarly, the variable magnification mechanism 50Rd moves at least one of the plurality of zoom lenses 51 to 53 of the zoom expander for right eye 50R in the optical axis direction (direction along the optical axis). The main controller 201 changes the magnification ratio of the observation optical system for right eye 40R by controlling the variable magnification mechanism 50Rd.

Controls for the operation device 2 include an operation permission control, an operation prohibition control, an operation signal transmission control and/or an operation signal reception control from the operation device 2, and other controls. The main controller 201 receives an operation signal generated by the operation device 2 and executes a control corresponding to the operation signal received.

Controls for the display device 3 include an information display control and other controls. As a display controller, the main controller 201 displays an image based on digital image data generated by the image sensor 62 on the display device 3. Typically, the main controller 201 may display a pair of moving images (a pair of videos, a pair of movies) in parallel based on a pair of moving image data (video signals) respectively generated in parallel by the image sensor 62 on the display device 3. Further, the main controller 201 may display a still image (frame) included in one of the pair of moving images on the display device 3. In addition, the main controller 201 may display an image (a moving image, a still image, etc.) obtained by processing the digital image data generated by the image sensor 62 on the display device 3. Furthermore, the main controller 201 may display, on the display device 3, any information generated by the ophthalmic observation apparatus 1, any information acquired from the outside by the ophthalmic observation apparatus 1, and other types of information.

The main controller 201 may display a moving image for left eye by sequentially displaying, on the display device 3, digital image data (frames) that are sequentially generated as moving image data for left eye by the image sensor 62 of the observation optical system for left eye 40L, while displaying a moving image for right eye by sequentially displaying, on the display device 3, digital image data (frames) that are sequentially generated as moving image data for right eye by the image sensor 62 of the observation optical system for right eye 40R. Here, the left image sensor 62 and the right image sensor 62 may be operated in synchronization with each other, and the display of the moving image for left eye and the display of the moving image for right eye may be operated in synchronization with each other. As a result of this, the ophthalmic observation apparatus 1 can substantially simultaneously display a left frame and a right frame that are substantially simultaneously obtained by the left image sensor 62 and the right image sensor 62 on the display device 3, thereby synchronizing between updating operations of left and right displays.

The moving image data acquired by the observation optical system 40 may be processed by the data processor 210 and then displayed on the display device 3 by the main controller 201. The data processor 210 may sequentially apply predetermined processing (image processing) to digital image data (frames) that are sequentially generated as moving image data for left eye by the image sensor 62 of the observation optical system for left eye 40L, while sequentially applying predetermined processing (image processing) to digital image data (frames) that are sequentially generated as moving image data for right eye by the image sensor 62 of the observation optical system for right eye 40R. Here, the left image sensor 62 and the right image sensor 62 may be operated in synchronization with each other, and the processing of the moving image data for left eye and the processing of the moving image data for right eye may be executed in synchronization with each other. In other words, the data processor 210 may execute parallel processing (simultaneous processing) of left and right frames that are substantially simultaneously obtained by the left and right image sensors 62. The left and right frames processed in parallel are sent to the main controller 201 as a pair of frames, that is, as frames associated with each other, for example. The main controller 201 receives such pairs of frames (frames for left eye and frames for right eye) sequentially input from the data processor 210, and may display a moving image for left eye by sequentially displaying on the display device 3 the frames for left eye that are sequentially input, and also at the same time, display a moving image for right eye by sequentially displaying on the display device 3 the frames for right eye that are sequentially input. Here, the display of the moving image for left eye and the display of the moving image for right eye may be executed in synchronization with each other. With this, the ophthalmic observation apparatus 1 can execute parallel processing of frames obtained substantially simultaneously by the left and right image sensors 62, and also at the same time, substantially simultaneously display the frames on the display device 3, thereby synchronizing between updating operations of left and right displays.

The main controller 201 may be configured to display a moving image for left eye and a moving image for right eye on the display device 3 in such a manner as to enable stereoscopic vision. For example, the main controller 201 may create a pair of left and right parallax images from the frame for left eye and the frame for right eye that have been obtained substantially simultaneously, and then display the pair of parallax images on the display device 3. With this, the user (e.g., surgeon) can recognize the pair of parallax images as a stereoscopic image by using a known stereoscopic method or technique. The stereoscopic method applicable to the present aspect may be freely selected, and for example, may be any of the following methods: a stereoscopic method for naked eyes; a stereoscopic method using an auxiliary device (polarized glasses, etc.); a stereoscopic method by applying image processing (image synthesis, image composition, rendering, etc.) to a frame for left eye and a frame for right eye; a stereoscopic method by displaying a pair of parallax images simultaneously; a stereoscopic method by alternately displaying a pair of parallax images; and a stereoscopic method of a combination of two or more of the above methods.

The data processor 210 executes various kinds of data processes. Some examples of processing that may be executed by the data processor 210 will be described below. The data processor 210 (each element thereof) includes a processor that operates on the basis of predetermined software (program), and is implemented by the cooperation of hardware and software. The data processor 210 acts as a focus processor together with the controller 200 (the main controller 201).

The ophthalmic observation apparatus 1 of the present embodiment is configured to perform photography while projecting a plurality of indicators onto the subject's eye E using illumination light, perform detection of a plurality of indicator images from an image acquired (moving image data, frame), and perform a focus control of the observation optical system 40. The data processor 210 is configured to perform processing for detecting the plurality of indicator images corresponding to the plurality of indicators from the image of the subject's eye E. The focus control executed on the basis of the plurality of indicator images detected is carried out by the main controller 201 controlling the movement mechanism 70.

The data processor 210 is configured to perform the detection of the indicator images from the image by means of a freely selected or determined method or technique of image region extraction. In the image region extraction process, the data processor 210 may perform indicator image detection in accordance with a processing procedure that has been created in consideration of the aspects (appearances) and/or arrangements of individual indicators provided in the indicator member 35.

Several examples of the indicator image detection having the visual aspects of the indicators taken into consideration will be described. The facts are taken into consideration that an indicator image is depicted relatively dark in the case where the corresponding indicator is a reticle and that an indicator image is depicted relatively bright in the case where the corresponding indicator is a light source. Then, the data processor 210 may perform indicator image detection using brightness thresholding such as binarization. In the case where the color is a feature (characteristic) of an indicator, the data processor 210 may perform indicator image detection using color analysis processing such as feature color extraction. In the case where the shape is a feature (characteristic) of an indicator, the data processor 210 may perform indicator image detection using shape analysis processing such as pattern matching. The data processor 210 may be configured to perform indicator image detection using a freely selected or designed segmentation method or technique. It is widely known that segmentation is image processing of identifying a partial region of an image. The segmentation of the present embodiment may include any known image processing technique. For example, the segmentation of the present embodiment may include segmentation by means of image processing such as edge detection, and/or segmentation by means of machine learning (e.g., deep learning) may be included.

In the case of taking the arrangements of the indicators into account, for example, the data processor 210 may be configured to determine a search area in an image frame based on the arrangement of an indicator provided in the indicator member 35. In some examples, options of the search area may be determined in advance according to the arrangement of the optical system. In the case where the arrangement of the optical system can be changed, the data processor 210 may determine a search area corresponding to the current arrangement of the optical system based on a search area determined in advance for a default arrangement of the optical system and the current arrangement of the optical system.

<Automatic Focusing>

Several examples of the operation (automatic focusing, automatic focus adjustment) of the ophthalmic observation apparatus 1 of the present embodiment will be described. It should be noted that while the operation examples below are described for the case in which the observation mode is switched from the anterior eye segment observation mode to the posterior eye segment observation mode, the same or similar operation can be performed for the case of other mode switching aspects. For example, those skilled in the art will appreciate that the same or similar operation can be performed in the case of switching the observation mode from the posterior eye segment observation mode to the anterior eye segment observation mode or in any other cases.

The first example of the operation of the ophthalmic observation apparatus 1 will be described. The case to be considered and described here is that the observation mode is switched from the anterior eye segment observation mode, in which the observation plane is located on the cornea Ec (i.e., in which the cornea Ec and the image sensor 62 are in an optically conjugate relationship), to the posterior eye segment observation mode. As mentioned above, the shift from the anterior eye segment observation mode to the posterior eye segment observation mode is made by inserting the front lens 21 between the objective lens 20 and the subject's eye E.

In some aspect examples, the ophthalmic observation apparatus 1 is capable of automatically detecting an event that the front lens 21 has been inserted into the optical path. For example, when the user performs an operation of inserting the front lens 21 into the optical path, the ophthalmic observation apparatus 1 detects, by means of an encoder or a microswitch which is not shown in the drawings of the present disclosure, movement of a member (such as an arm) that supports the front lens 21, and then starts executing processing related to a focus control. In another example in which the main controller 201 is configured to execute a control to insert the front lens 21 into the optical path, the ophthalmic observation apparatus 1 may further be configured to start executing processing related to a focus control subsequently to the execution of the control for insertion of the front lens 21. In yet another example, the ophthalmic observation apparatus 1 may be configured to be capable of detecting an event that the observation mode is changed from the anterior eye segment observation mode to the posterior eye segment observation mode, based on a change in a moving image caused by the insertion of the front lens 21 into the optical path.

The first step of the processing related to the focus control in the present example is to execute a process of providing the plurality of indicators by means of the indicator member 35. In some aspect examples, the indicator member 35 is inserted into the optical path of the second illumination optical system 32 under the control of the main controller 201. Alternatively, the plurality of indicators is displayed on the aforementioned light transmissive display serving as the indicator member 35 under the control of the main controller 201.

Next, the main controller 201 turns on the light source 32a of the second illumination optical system 32. With this, the illumination light output from the light source 32a is projected onto the subject's eye E via the indicator member 35. The observation optical system 40 acquires an image (moving image, video) in which a plurality of indicator images corresponding to the plurality of indicators projected onto the subject's eye E is depicted. The main controller 201 sequentially transfers frames (still images) sequentially acquired as the moving image by the observation optical system 40, to the data processor 210.

The data processor 210 is configured to sequentially perform detection of the plurality of indicator images from individual frames sequentially input from the main controller 201. Now the case is considered in which the plurality of indicators includes two indicators that are arranged at positions away from the observation plane (e.g., retina) by optical distances different from each other. Then, blur states of the two indicator images corresponding to the two indicators are different from one another. For example, in the case where one of the two indicators is located on the light source 32a side (near the light source 32a) with respect to a position optically conjugate with the observation plane, and the other is located on the subject's eye E side (near the subject's eye E) with respect to the position optically conjugate with the observation plane, when the focal point of the observation optical system 40 is located on the front side of the observation plane (that is, located on the objective lens 20 side), then the degree of focus on the one indicator increases (that is, the other indicator is increasingly blurred). On the other hand, when the focal point of the observation optical system 40 is located on the back side of the observation plane, the degree of focus on the other indicator increases (that is, the one indicator is increasingly blurred). Note that when the focal point (almost) coincides with the observation plane, the degrees of blurring of the two indicator images become equivalent (almost the same, almost equal). For example, in the case where the sizes of the two indicators are designed to be the same, then the sizes of the two indicator images become almost the same when the focal point (almost) coincides with the observation plane. In this way, depending on the position of the focal point with respect to the observation plane, the indicator becoming in focus is reversed. Such phenomena can be used to know whether the focal point is located on the front side or on the back side with respect to the observation plane. It should be noted that any known blur quantification method can be employed to evaluate or assess the magnitude of blur.

As described thus far, the data processor 210 of the present example can determine the position of the focal point with respect to the observation plane based on the blur states of the plurality of indicator images, and then determine a movement direction of the surgical microscope 10 in order to match the focal point with the observation plane. In addition, the data processor 210 can determine a movement amount (movement distance) of the surgical microscope 10 in order to match the focal point with the observation plane based on the degrees of blurring of the plurality of indicator images (e.g., based on a comparison between the degrees of blurring of the plurality of indicator images).

At least one of the movement direction and the movement amount obtained by the data processor 210 is provided to the main controller 201 as movement control information. By controlling the movement mechanism 70 based on the movement control information, the main controller 201 can perform focus adjustment (focus control) to match the focal point of the observation optical system 40 with the observation plane (e.g., retina).

According to the first example performed in this manner, the amount of work for the user can be reduced, the operation time can be shortened, and the burdens on the user and the patient can be reduced.

Figure 5:
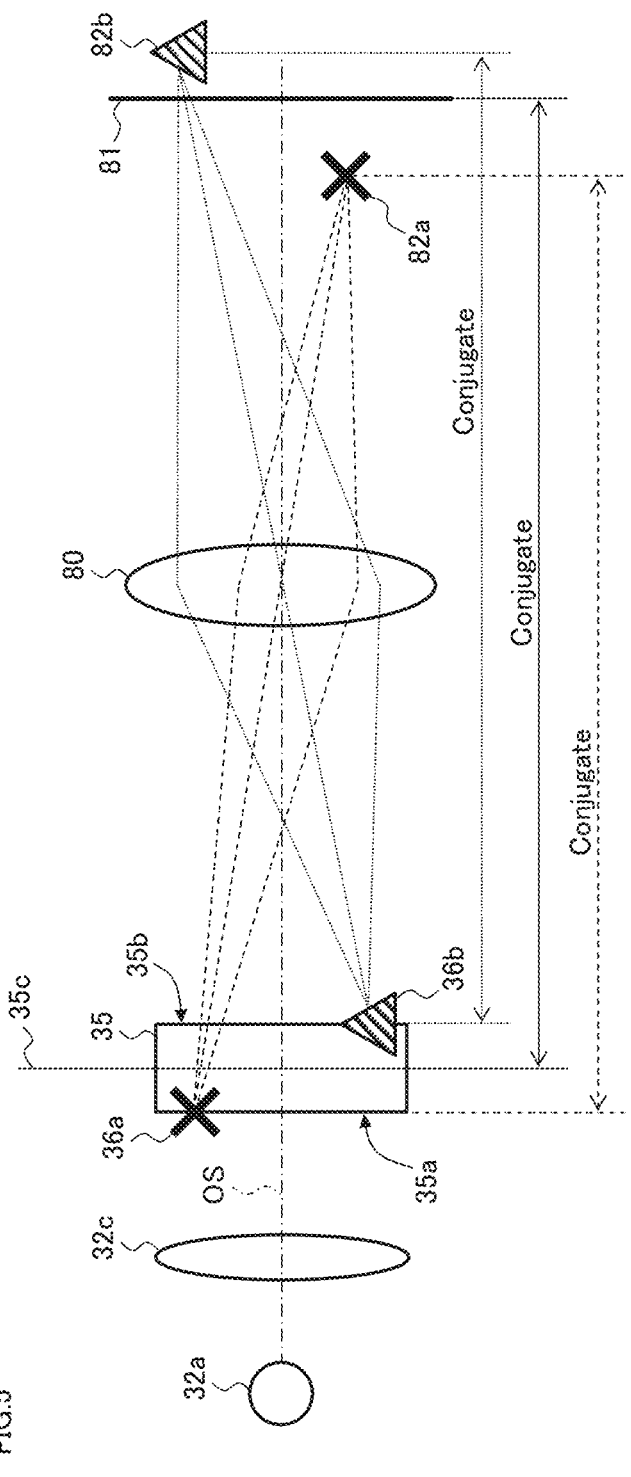
FIG. 5 is a diagram for describing an example of an operation of an ophthalmic observation apparatus according to an embodiment example.

The second example of the operation of the ophthalmic observation apparatus 1 will be described. As in the first example, the case to be considered and described here is that the observation mode is switched from the anterior eye segment observation mode to the posterior eye segment observation mode. FIG. 5 will be referred to. FIG. 5 shows a schematic diagram of the second illumination optical system 32.

The lens 32c is a condenser lens provided on the light source 32a (described above). The lens 32c acts as a collimator lens that converts the illumination light output from the light source device 32a into a collimated light beam.

The indicator member 35 in the present example is a plane parallel plate. The first indicator 36a is formed on the surface 35a of the plane parallel plate 35 on the light source 32a side, and the second indicator 36b is formed on the surface 35b parallel to the surface 35a (the surface 35b on the subject's eye E side). The aspect of the first indicator 36a and the aspect of the second indicator 36b are both freely designed or determined. For example, the shape of the first indicator 36a and the shape of the second indicator 36b may be the same (e.g., may be of a circular shape), and the size of the first indicator 36a and the size of the second indicator 36b may be the same. Note that in FIG. 5, the first indicator 36a and the second indicator 36b are represented by individually different figures in order to enhance their distinguishability for the sake of convenience.

The first indicator 36a is arranged at a position apart from the optical axis OS of the second illumination optical system 32 by the first distance in the first direction (e.g., upward in FIG. 5) perpendicular to the optical axis OS. The second indicator 36b is arranged at a position apart from the optical axis OS by the second distance in the second direction (e.g., downward in FIG. 5) perpendicular to the optical axis OS and different from the first direction. The first distance and the second distance may or may not be equal. The first direction and the second direction may or may not be opposite to each other with respect to the optical axis OS. In the present example, the case is to be considered and described in which the first distance and the second distance are equal, and the first direction and the second direction are directions opposite to each other with respect to the optical axis OS. In other words, in the present example, the first indicator 36a and the second indicator 36b are arranged at symmetric positions (arranged at point-symmetric positions) with respect to the optical axis OS in the direction perpendicular to the optical axis OS (in the XY direction).

The reference character 35c denotes the plane positioned at the same distance from both the first surface 35a and the second surface 35b. In other words, the plane 35c is the center plane of the plane parallel plate 35. The center plane is parallel to and at the same distance from both the first surface 35a and the second surface 35b. The plane 35c is in an optically conjugate relationship with the observation plane 81. The first indicator image 82a formed by the second illumination optical system 32 is an image of the first indicator 36a and is formed at a position optically conjugate with the first indicator 36a. Likewise, the second indicator image 82b formed by the second illumination optical system 32 is an image of the second indicator 36b and is formed at a position optically conjugate with the second indicator 36b.

The reference character 80 denotes a schematic aspect of an optical element group arranged between the plane parallel plate 35 and the observation plane 81 (e.g., retina). In the case where the optical system shown in FIG. 2 and FIG. 3 is employed, the optical element group 80 includes the lens 32b and the objective lens 20 in the anterior eye segment observation mode, and includes the lens 32, the objective lens 20, and the front lens 21 in the posterior eye segment observation mode.

The illumination light output from the light source 32a is converted into parallel light (collimated light) by the lens 32c, passes through the plane parallel plate 35 having the first indicator 36a and the second indicator 36b, and is projected onto the subject's eye E via the optical element group 80. By conducting photographing, by using the observation optical system 40, of the subject's eye E onto which such illumination light is being projected, an image (moving image) is obtained in which the first indicator image 82a and the second indicator image 82b are depicted. The present example uses such two indicator images 82a and 82b to determine a positional relationship between the focal point of the observation optical system 40 and the observation plane 81.

Figure 6A:
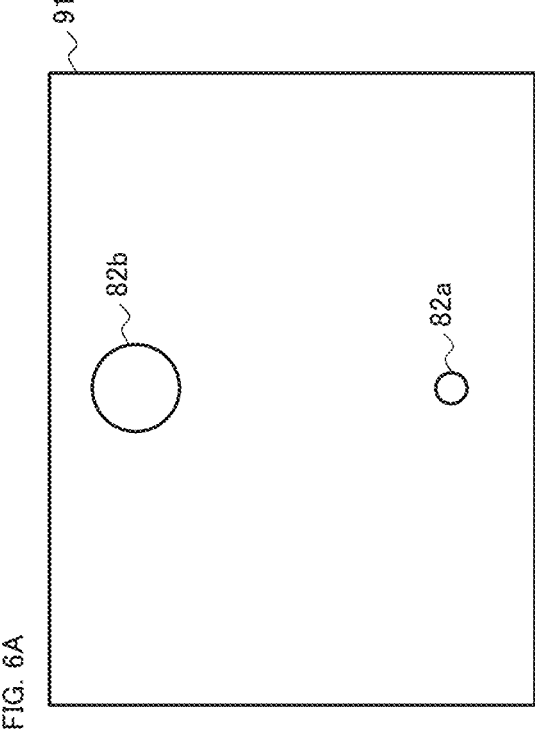
FIG. 6A is a diagram for describing an example of an operation of an ophthalmic observation apparatus according to an embodiment example.
Figure 6B:
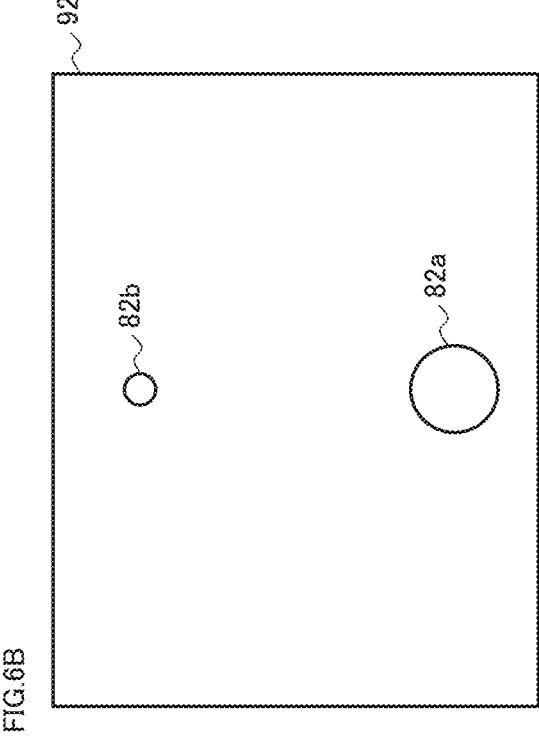
FIG. 6B is a diagram for describing an example of an operation of an ophthalmic observation apparatus according to an embodiment example.
Figure 6C:
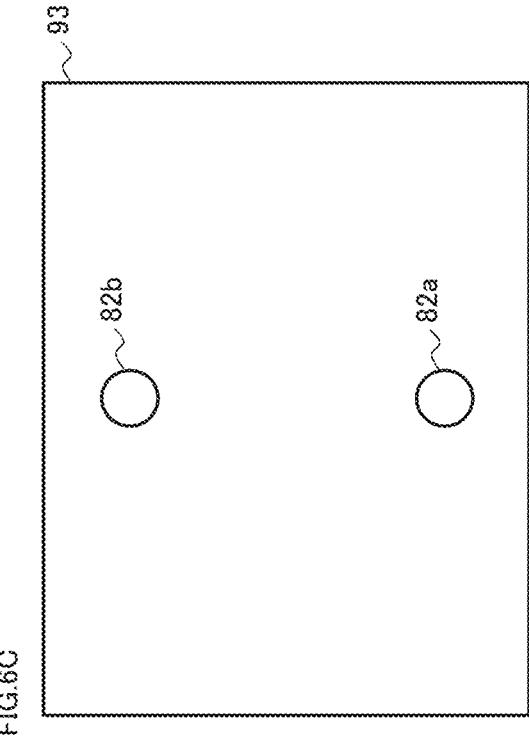
FIG. 6C is a diagram for describing an example of an operation of an ophthalmic observation apparatus according to an embodiment example.

FIG. 6A, FIG. 6B and FIG. 6C show examples of aspects of the first indicator image 82a and the second indicator image 82b depicted in the image (frame) acquired in the present example.

The image 91 shown in FIG. 6A is a schematic representation (schematic illustration) of an image acquired when the focal point of the observation optical system 40 is located on the front side (on the objective lens 20 side) of the observation plane 81. In this case, the position of the focal point of the observation optical system 40 is optically closer to the position where the first indicator image 82a is formed (the position optically conjugate with the first indicator 36a) than to the position where the second indicator image 82b is formed (the position optically conjugate with the second indicator 36b). Therefore, the first indicator image 82a in the image 91 has a relatively good focus state (the degree of blurring is relatively small), and the second indicator image 82b in the image 91 has a relatively poor focus state (the degree of blurring is relatively large). In other words, a comparison between the first indicator image 82a and the second indicator image 82b detected by the data processor 210 yields a result that the size of the first indicator image 82a is smaller than the size of the second indicator image 82b.

The image 92 shown in FIG. 6B is a schematic representation (schematic illustration) of an image acquired when the focal point of the observation optical system 40 is located on the back side (on the opposite side of the objective lens 20) of the observation plane 81. In this case, the position of the focal point of the observation optical system 40 is optically closer to the position where the second indicator image 82b is formed than to the position where the first indicator image 82a is formed. Therefore, the first indicator image 82a in the image 92 has a relatively poor focus state (the degree of blurring is relatively large), and the second indicator image 82b of the image 92 has a relatively good focus state (the degree of blurring is relatively small). In other words, a comparison between the first indicator image 82a and the second indicator image 82b detected by the data processor 210 yields a result that the size of the first indicator image 82a is larger than the size of the second indicator image 82b.

The image 93 shown in FIG. 6C is a schematic representation (schematic illustration) of an image acquired when the focal point of the observation optical system 40 (almost) coincides with the observation plane 81. In this case, the distance from the position of the focal point of the observation optical system 40 to the position where the first indicator image 82a is formed is optically (almost) the same as the distance from the position of the focal point of the observation optical system 40 to the position where the second indicator image 82b is formed. Therefore, the focus state of the first indicator image 82a and the focus state of the second indicator image 82b in the image 93 are equivalent in this case. In other words, a comparison between the first indicator image 82a and the second indicator image 82b detected by the data processor 210 yields a result that the size of the first indicator image 82a and the size of the second indicator image 82b are almost the same.

As can be seen from the above description, according to the present example, the focus state of the observation optical system 40 can be known on the basis of the sizes of the two indicator images. Note that the number of indicators used is not limited to two, and may be three or more.

When the sizes of the two indicator images are different from one another, the ophthalmic observation apparatus 1 of the present example is capable, by the data processor 210, of knowing the fact (the state) that the focal point of the observation optical system 40 is off the observation plane, that is, the focus state is not satisfactory. Furthermore, the ophthalmic observation apparatus 1 of the present example is capable of performing focus adjustment by moving the surgical microscope 10 through a control of the movement mechanism 70 executed by the main controller 201. Note that in the case where the observation optical system 40 is provided with a focus lens, the position of the focus lens can be adjusted. The data processor 210 can determine a movement direction of the surgical microscope 10 by obtaining a relationship between the sizes of the two indicator images. The data processor 210 can also determine a movement amount of the surgical microscope 10 based on the difference (e.g., a result of subtraction, ratio, etc.) between the sizes of the two indicator images. Based on the movement control information generated in this way, the main controller 201 can perform a control of the movement mechanism 70. Repetitive execution of such a series of processes allows the focal point of the observation optical system 40 to be guided to the observation plane, and further allows the favorable focus state achieved in this way to be maintained.

In some aspect examples, the ophthalmic observation apparatus 1 may be configured to perform the following processes: a process of analyzing an observation image acquired by the surgical microscope 10 to detect a plurality of indicator images; a process of calculating the size (e.g., diameter, circumference) of each indicator image detected; a process of comparing the calculated sizes of the plurality of indicator images; a process of generating movement control information (movement direction, movement amount (movement distance)) based on a result of the size comparison; and a process of moving the surgical microscope 10 (or a focus lens) based on the movement control information generated. Furthermore, in some aspect examples, the ophthalmic observation apparatus 1 may be configured to repeatedly perform such a series of processes until the sizes of a plurality of indicator images detected satisfy a predetermined condition. For example, the ophthalmic observation apparatus 1 may be configured to repeatedly perform the above series of processes until the sizes of a plurality of indicator images detected become equivalent sizes to each other, such as until the sizes of the plurality of indicator images detected become equal, or until the differences in size between the plurality of indicator images detected become equal to or less than a predetermined threshold value.

Some aspect examples may be configured to perform a focus control in response to an operation of switching observation sites. For example, the ophthalmic observation apparatus 1 may further include a mode switching unit configured to perform an observation mode switching between the first observation mode for observing the first site of the subject's eye E and the second observation mode for observing the second site that is different from the first site. In addition, the controller 200 and the data processor 210 (focus processor) may be configured to perform the detection of a plurality of indicator images and a focus control in response to an event that the mode switching unit performs observation mode switching. According to this aspect example, an operation of switching the observation mode can be used as a trigger to start automatic focusing of any of the aspect examples described above.

As mentioned above, the first observation mode may be the anterior eye segment observation mode, and the second observation mode may be the posterior eye segment observation mode. If this is the case, the mode switching unit may include the front lens 21 that is inserted into the optical path in order to switch from the anterior eye segment observation mode to the posterior eye segment observation mode. The ophthalmic observation apparatus 1 can start an automatic focusing operation (can activate an automatic focusing function) of any of the aspect examples described above by using an operation of inserting the front lens 21 into the optical path as a trigger. Further, the ophthalmic observation apparatus 1 may also be configured to start automatic focusing of any of the aspect examples described above by using an operation of removing the front lens 21 from the optical path as a trigger.

In place of performing automatic focusing, or in addition to performing automatic focusing, the ophthalmic observation apparatus 1 may display information representing the focus state acquired by the data processor 210. This allows the user to grasp the current focus state from the information displayed.

In place of performing automatic focusing, or in addition to performing automatic focusing, the ophthalmic observation apparatus 1 may display information representing the movement control information (movement direction, movement amount) acquired by the data processor 210. This allows the user to perform manual focus adjustment (fine adjustment operation, etc.) while referring to the information displayed. In other words, the ophthalmic observation apparatus 1 configured in this way can assist manual focus adjustment operations.

<Alignment>

Some aspect examples of automatic focusing described above correspond to alignment of the surgical microscope 10 in the Z direction. In addition to this, the ophthalmic observation apparatus 1 is capable of performing alignment of the surgical microscope 10 in the XY direction.

Conventionally, a surgeon moves a surgical microscope to prevent unwanted light or dark areas from entering the field of view while referring to an observation image (e.g., while observing a displayed image or while observing a subject's eye through the eyepiece). The operation for that purpose is performed using a foot switch or a lever provided on the surgical microscope.

Several examples of alignment in the XY directions will be described below. It should be noted that it is possible to combine at least two of the several examples described below at least in part. In addition, in the following description, the matters and items related to the ophthalmic observation apparatus 1 described above will be referred to as appropriate.

For alignment in the XY direction, at least part of the illumination optical system 30 and at least part of the observation optical system 40 are moved in the XY direction. This movement is performed by the main controller 201 controlling the movement mechanism 70.

The ophthalmic observation apparatus 1 may be configured to perform alignment by moving the front lens 21 when the front lens 21 is in the optical path, and to perform alignment by moving the objective lens 20 when the front lens 21 is out of the optical path.

In a wider sense, the ophthalmic observation apparatus 1 may be configured to perform alignment by any one of the following actions or a combination of any two or more of the following actions: movement of at least one or more of the elements of the illumination optical system 30; movement of at least one or more of the elements of the observation optical system 40; movement of the objective lens and movement of the front lens 21.

Figure 7:
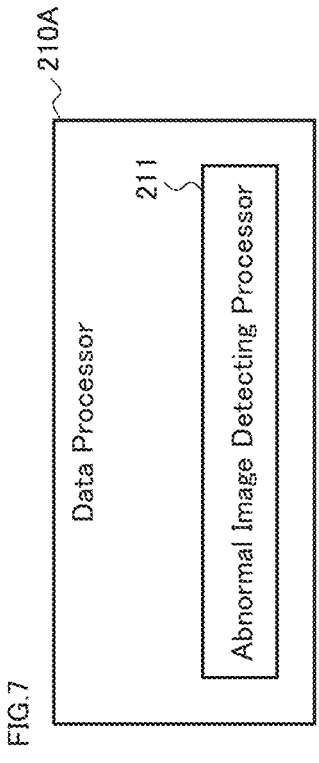
FIG. 7 is a diagram illustrating an example of a configuration of an ophthalmic observation apparatus according to an embodiment example.

FIG. 7 shows a configuration example of the first aspect for implementing automatic alignment in the XY direction. The data processor 210A of the present example is an example of the data processor 210 and includes the abnormal image detecting processor 211. The abnormal image detecting processor 211 is configured to perform image analysis to perform detection of an abnormal image from an image acquired by the observation optical system 40. The abnormal image is, for example, an image region that has abnormally high brightness (e.g., an image of unwanted light such as flare), an image region that has abnormally low brightness (dark area), or the like. The abnormal image detecting processor 211 of some examples may be configured to perform abnormal image detection by means of brightness thresholding.

The controller 200 (the main controller 201) and the data processor 210 function as a movement processor and perform a control of the movement mechanism 70 based on the abnormal image detected by the abnormal image detecting processor 211 to move the surgical microscope 10 in the XY direction.

Figure 8:
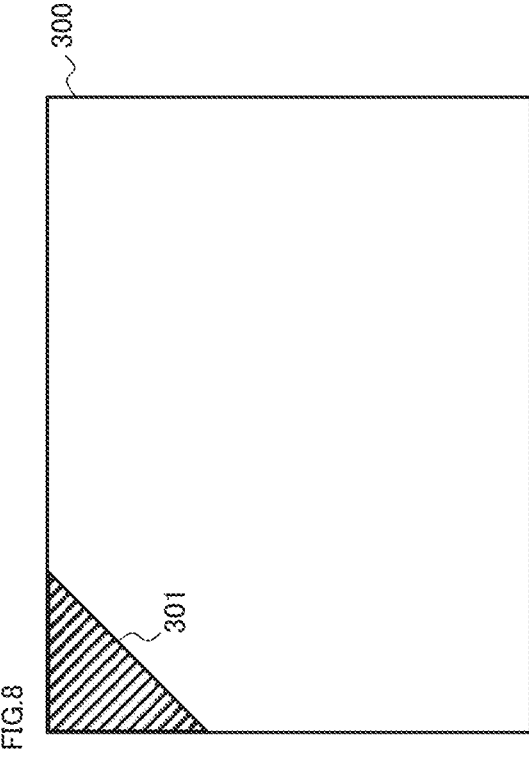
FIG. 8 is a diagram for describing an example of an operation of an ophthalmic observation apparatus according to an embodiment example.

The image 300 shown in FIG. 8 is a schematic representation (schematic illustration) of an image that includes an abnormal image. The reference character 301 denotes an abnormal image (e.g., flare or dark area) detected from the image 300 by the abnormal image detecting processor 211. The data processor 210 may determine a movement direction based on the position of the abnormal image 301 in the image 300 (in the image frame). For example, in the image 300 of FIG. 8, the abnormal image 301 is located in the upper left corner region of the image frame. In this case, the data processor 210 may set the lower right corner direction to be the movement direction. In a wider sense, the data processor 210 may set the direction opposite to the direction in which an abnormal image exists when viewed from the image center (with respect to the image center), to be the movement direction. In some examples, the data processor 210 may be configured to perform the following series of processes: a process of finding a representative point of an abnormal image; a process of calculating a vector whose initial point is at the representative point and whose terminal point is at the image center; and a process of setting the direction of the vector to the movement direction. The representative point of the abnormal image may be, for example, the position of the center of gravity of the abnormal image, or the position of a point(s) in the abnormal image that is(are) closest to the image center.

The data processor 210 may determine a movement amount based on the size of the abnormal image 301 in the image 300. For example, the data processor 210 may be configured to perform the following series of processes: a process of identifying the position of a point in the abnormal image that is closest to the image center; a process of calculating a vector whose initial point is at the intersection of the frame edge and the straight line that passes through both the identified position and the image center and whose terminal point is at the identified position; and a process of setting the magnitude of the vector (or a value larger than the magnitude of the vector) to be the movement amount. In this case, the direction of the vector may be set as the movement direction.

The main controller 201 may perform alignment of the surgical microscope 10 in the XY direction by controlling the movement mechanism 70 based on the movement control information (movement direction, movement amount) generated by the data processor 210. It should be noted that the optimum position in the XY direction can be searched by repeatedly performing the acquisition of the movement control information and the movement of the surgical microscope 10.

According to the automatic alignment performed in this manner, the amount of work for the user can be reduced, the operation time can be shortened, and the burden on the user and the patient can be reduced, compared to conventional manual alignment.

Figure 9:
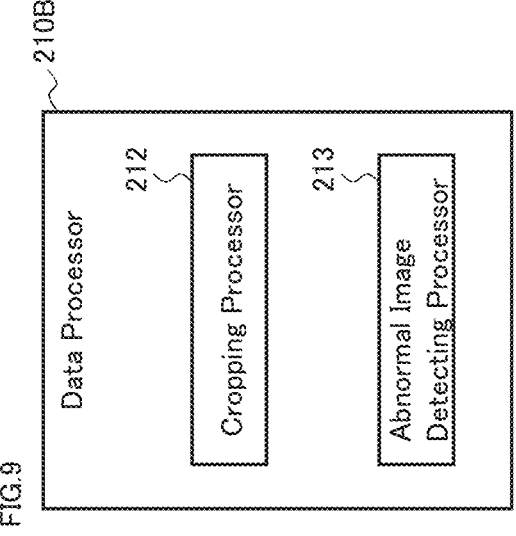
FIG. 9 is a diagram illustrating an example of a configuration of an ophthalmic observation apparatus according to an embodiment example.

FIG. 9 shows a configuration example of the second aspect for implementing automatic alignment in the XY direction. The data processor 210B of the present example is an example of the data processor 210 and includes the cropping processor 212 and the abnormal image detecting processor 213.

The cropping processor 212 is configured to perform cropping of a region of a predetermined size from an image acquired by the observation optical system 40. Here, the region of the predetermined size to be cropped is referred to as a cropping target region. The size of the cropping target region may be fixed or variable. Also, a default position of the cropping target region may be fixed or variable. The main controller 201 displays an image (partial image)

cropped from the image obtained by the observation optical system 40 on the display device 3.

The abnormal image detecting processor 213 is configured to perform image analysis to perform detection of an abnormal image from the partial image cropped from the image obtained by the observation optical system 40. The abnormal image detecting processor 213 may be configured to execute the same or similar processing as or to the abnormal image detecting processor 211 of the first example.

If the abnormal image detecting processor 213 detects an abnormal image from the cropped partial image, the cropping processor 212 sets a new region of the predetermined size within a region in this image (i.e., in the image acquired by the observation optical system 40) that does not include the detected abnormal image. Note that the cropping processor 212 may change an aspect (e.g., size, shape, etc.) of a cropping target region in such a manner that a new cropping target region does not include the detected abnormal image.

Figure 10A:
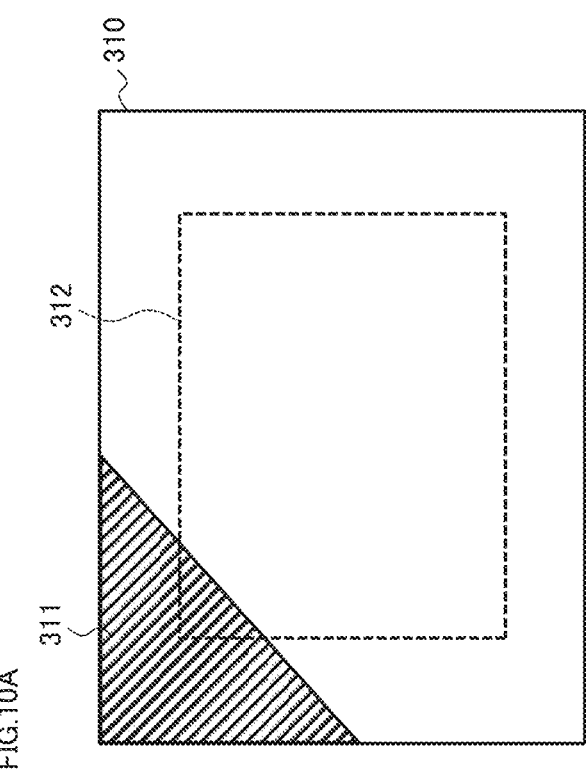
FIG. 10A is a diagram for describing an example of an operation of an ophthalmic observation apparatus according to an embodiment example.

The image 310 shown in FIG. 10A is a schematic representation (schematic illustration) of an image that includes an abnormal image. The image 310 is an image acquired by the observation optical system 40 and shows the entire imaging area of the image sensor 62. The reference character 311 denotes an abnormal image contained in the image 310. The reference character 312 denotes the cropping target region at the current stage. The cropping processor 212 performs extraction of the cropping target region 312 from the image 311. The cropping target region 312 is also referred to as the partial image 312. The abnormal image detecting processor 213 performs image analysis to perform detection of an abnormal image from the partial image 312. In the example shown in FIG. 10A, the partial image 312 includes a part of the abnormal image 311. In this case, the cropping processor 212 moves a cropping target region to a position within a region of the partial image 312 that does not contain the abnormal image detected. The process of determining a movement direction and a movement amount may be performed in the same or similar manner as or to the first example. In some examples, abnormal image detection may be applied to the entire image 311, and then a result of this abnormal image detection may be used for a movement operation of a cropping target region.

Figure 10B:
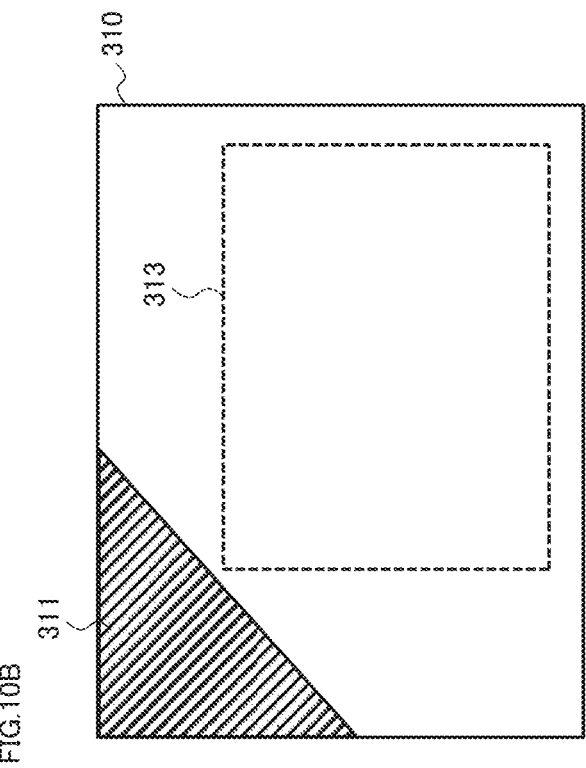
FIG. 10B is a diagram for describing an example of an operation of an ophthalmic observation apparatus according to an embodiment example.

FIG. 10B shows the cropping target region 313 moved by such automatic alignment. The cropping target region 313 after the movement does not include an abnormal image. It should be noted that a search for an optimum cropping target region can be carried out by repeatedly performing acquisition of movement control information (movement direction, movement amount) and movement of a cropping target region.

According to the automatic alignment performed in this manner, the amount of work for the user can be reduced, the operation time can be shortened, and the burden on the user and the patient can be reduced, compared to conventional manual alignment.

The embodiments described in the present disclosure are merely examples, and any modification, omission, addition, substitution, etc. can be made within the scope of the present disclosure and its equivalents.

What is claimed is:

1. An ophthalmic observation apparatus comprising:
   an illumination system that includes a light source configured to emit illumination light and an indicator member having a plurality of indicators and is configured to project the illumination light onto a subject's eye via the indicator member;

a photography system that includes an image sensor and is configured to perform photography of the subject's eye; and a focus processor configured to perform detection of a plurality of indicator images from an image acquired by the photography system and perform a focus control of the photography system based on the plurality of indicator images, wherein at least two indicators of the plurality of indicators are provided on a single member, the single member is a plane parallel plate that transmits the illumination light, and the plurality of indicators includes a first indicator provided on a first surface of the plane parallel plate and a second indicator provided on a second surface parallel to the first surface.

2. The ophthalmic observation apparatus according to claim 1, wherein the plurality of indicators includes two indicators arranged at positions away from an observation plane by optical distances different from each other.

3. The ophthalmic observation apparatus according to claim 2, wherein one of the two indicators is arranged on a side of the light source with respect to a position optically conjugate with the observation plane, and the other is arranged on a side of the subject's eye with respect to the position optically conjugate with the observation plane.

4. The ophthalmic observation apparatus according to claim 1, wherein at least one of the plurality of indicators is arranged off an optical axis of the illumination system.

5. The ophthalmic observation apparatus according to claim 4, wherein the plurality of indicators includes at least two indicators that have a same distance from the optical axis.

6. The ophthalmic observation apparatus according to claim 5, wherein the at least two indicators include two indicators arranged at symmetric positions with respect to the optical axis in a direction perpendicular to the optical axis.

7. The ophthalmic observation apparatus according to claim 1, wherein a position optically conjugate with an observation plane is arranged between the first surface and the second surface.

8. The ophthalmic observation apparatus according to claim 7, wherein the position optically conjugate with the observation plane is arranged at a position that has a same distance from both the first surface and the second surface.

9. The ophthalmic observation apparatus according to claim 1, wherein the focus processor is configured to perform the focus control based on sizes of the plurality of indicator images.

10. The ophthalmic observation apparatus according to claim 9, wherein the focus processor is configured to perform a comparison between the sizes of the plurality of indicator images and perform the focus control based on a result of the comparison.

11. The ophthalmic observation apparatus according to claim 10, further comprising:

an objective lens; and a first movement mechanism configured to move the illumination system and the photography system in a direction along an optical axis of the objective lens, wherein the focus processor is configured to perform generation of movement control information that includes at least one of a movement direction and a movement distance based on the result of the comparison and perform a control of the first movement mechanism based on the movement control information.

12. The ophthalmic observation apparatus according to claim 10, wherein the plurality of indicators includes a pair of indicators of a same size that are arranged at two positions respectively, the two positions being apart from a position optically conjugate with an observation plane by a same optical distance in mutually opposite directions in a direction along the optical axis of the illumination system, and the focus processor is configured to perform the focus control in such a manner as to equalize sizes of two indicator images corresponding to the pair of indicators.

13. The ophthalmic observation apparatus according to claim 1, wherein the focus processor is configured to perform the focus control based on blurring of the plurality of indicator images.

14. The ophthalmic observation apparatus according to claim 1, further comprising:

an objective lens;

a second movement mechanism configured to move the illumination system and the photography system in a direction perpendicular to an optical axis of the objective lens;

an abnormal image detecting processor configured to perform image analysis to detect an abnormal image from the image acquired by the photography system; and a movement processor configured to perform a control of the second movement mechanism based on the abnormal image when the abnormal image is detected by the abnormal image detecting processor.

15. The ophthalmic observation apparatus according to claim 1, further comprising:

a cropping processor configured to perform cropping of a region of a predetermined size from the image acquired by the photography system; and an abnormal image detecting processor configured to perform image analysis to perform detection of an abnormal image from a partial image obtained by the cropping from the image, wherein the cropping processor is configured to move the region of the predetermined size to a region in the image that does not include the abnormal image when the abnormal image is detected by the abnormal image detecting processor.

16. The ophthalmic observation apparatus according to claim 1, further comprising a mode switching unit configured to perform switching between a first observation mode for observing a first site of the subject's eye and a second observation mode for observing a second site that is different from the first site, wherein the focus processor is configured to perform the detection of the plurality of indicator images and the focus control in response to performance of observation mode switching by the mode switching unit.

17. The ophthalmic observation apparatus according to claim 16, wherein the first observation mode is an anterior eye segment observation mode for observing an anterior eye segment of the subject's eye, the second observation mode is a posterior eye segment observation mode for observing a posterior eye segment of the subject's eye, and the mode switching unit includes a lens that is inserted into an optical path in order to switch from the anterior eye segment observation mode to the posterior eye segment observation mode.

\* \* \* \* \*